(12) United States Patent
Maruo

(10) Patent No.: US 9,407,922 B2
(45) Date of Patent: Aug. 2, 2016

(54) SYSTEM AND METHOD OF MANAGING MEDICAL IMAGE

(71) Applicant: FUJIFILM Corporation, Tokyo (JP)

(72) Inventor: Yusuke Maruo, Tokyo (JP)

(73) Assignee: Fujifilm Corporation, Tokyo (JP)

(*) Notice: Subject to any disclaimer, the term of this patent is extended or adjusted under 35 U.S.C. 154(b) by 0 days.

(21) Appl. No.: 14/663,356

(22) Filed: Mar. 19, 2015

(65) Prior Publication Data
US 2015/0195542 A1 Jul. 9, 2015

Related U.S. Application Data

(63) Continuation of application No. PCT/JP2013/074802, filed on Sep. 13, 2013.

(30) Foreign Application Priority Data

Sep. 26, 2012 (JP) ................................. 2012-212592

(51) Int. Cl.
G06K 9/36 (2006.01)
H04N 19/156 (2014.01)
(Continued)

(52) U.S. Cl.
CPC ............ H04N 19/156 (2014.11); G06F 19/321 (2013.01); H04L 43/00 (2013.01);
(Continued)

(58) Field of Classification Search
CPC ....... H04N 19/156; H04L 67/04; B41M 5/24; B41M 5/42; B41M 5/426; G03C 5/17; G06F 19/321; G06F 19/322; G06F 19/324
USPC .......................................................... 382/232
See application file for complete search history.

(56) References Cited

U.S. PATENT DOCUMENTS

2008/0021834 A1* 1/2008 Holla et al. ...................... 705/51
2012/0075168 A1* 3/2012 Osterhout et al. ................. 345/8
2014/0276030 A1* 9/2014 McCollough et al. ........ 600/430

FOREIGN PATENT DOCUMENTS

JP 2000-293528 A 10/2000
JP 2003-116082 A 4/2003
(Continued)

OTHER PUBLICATIONS

International Search Report in [PCT/JP2013/074802] dated [Dec. 17, 2013] (English-version).

Primary Examiner — Ali Bayat
(74) Attorney, Agent, or Firm — McGinn IP Law Group, PLLC

(57) ABSTRACT

In a medical image managing system, there are first and second density conversion modes. In the first density conversion mode, a medical image is processed in density conversion by an image server, before a density-converted medical image is transmitted to a client terminal. In the second density conversion mode, a medical image is transmitted from the image server to the client terminal, which processes the medical image in the density conversion. A density conversion mode checker compares processing time of the first density conversion mode with processing time of the second density conversion mode after acquisition according to communication speed between the image server and the client terminal, and processing speeds of the client terminal and the image server. One of the density conversion modes with the shorter processing time is selected. Thus, the density-converted medical image can be displayed rapidly at the client terminal.

16 Claims, 21 Drawing Sheets

(51) Int. Cl.
*G06F 19/00* (2011.01)
*H04L 29/08* (2006.01)
*H04L 12/26* (2006.01)

(52) U.S. Cl.
CPC ............. *H04L 67/04* (2013.01); *H04L 67/289* (2013.01); *H04L 67/2823* (2013.01); *H04L 67/2895* (2013.01); *H04L 67/12* (2013.01)

(56) References Cited

FOREIGN PATENT DOCUMENTS

| | | |
|---|---|---|
| JP | 2003-198940 A | 7/2003 |
| JP | 2011-098025 A | 5/2011 |
| JP | 2012-100899 A | 5/2012 |
| WO | WO 2006/087895 A1 | 8/2006 |

\* cited by examiner

F I G . 7
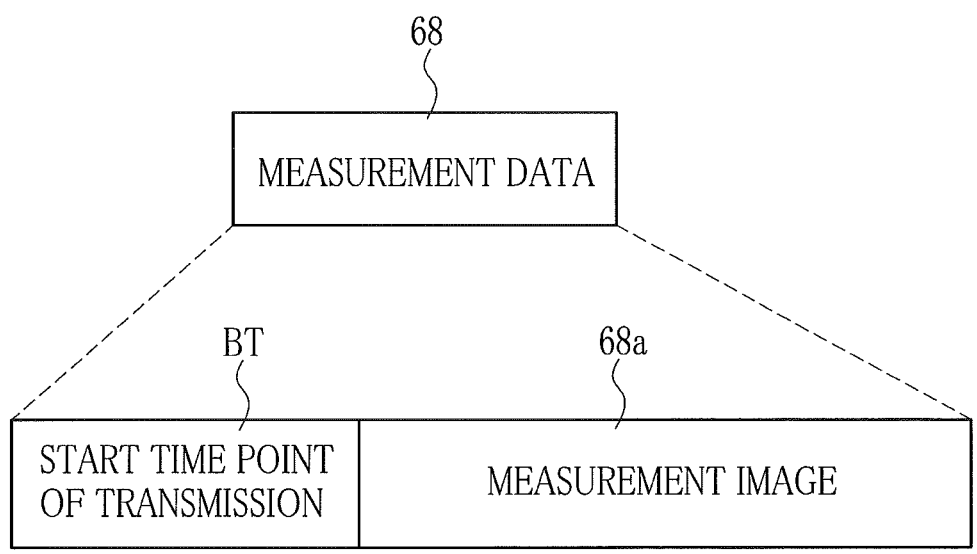

FIG. 8

| COMMUNICATION SPEED BETWEEN IMAGE SERVER & IMAGE DIAGNOSIS APPARATUS OF INSTALLED TYPE | CS1 |
|---|---|
| COMMUNICATION SPEED BETWEEN IMAGE SERVER & PORTABLE TERMINAL APPARATUS CONNECTED TO WIRELESS LAN | CS2 |
| COMMUNICATION SPEED BETWEEN IMAGE SERVER & PORTABLE TERMINAL APPARATUS CONNECTED TO MOBILE TELEPHONE LINE | CS3 |
| PROCESSING SPEED OF IMAGE DIAGNOSIS APPARATUS OF INSTALLED TYPE | PS1 |
| PROCESSING SPEED OF PORTABLE TERMINAL APPARATUS | PS2 |
| PROCESSING SPEED OF IMAGE SERVER | PS3 |

FIG. 16

| BROWSER NAME | TYPE NAME | PROCESSING SPEED (bps) |
|---|---|---|
| AA browser | ABC TABLET | ***** |
| BB browser | BBA PHONE | ***** |
| CC browser | CCB TABLET | ***** |
| DD browser | SSJ PHONE | ***** |

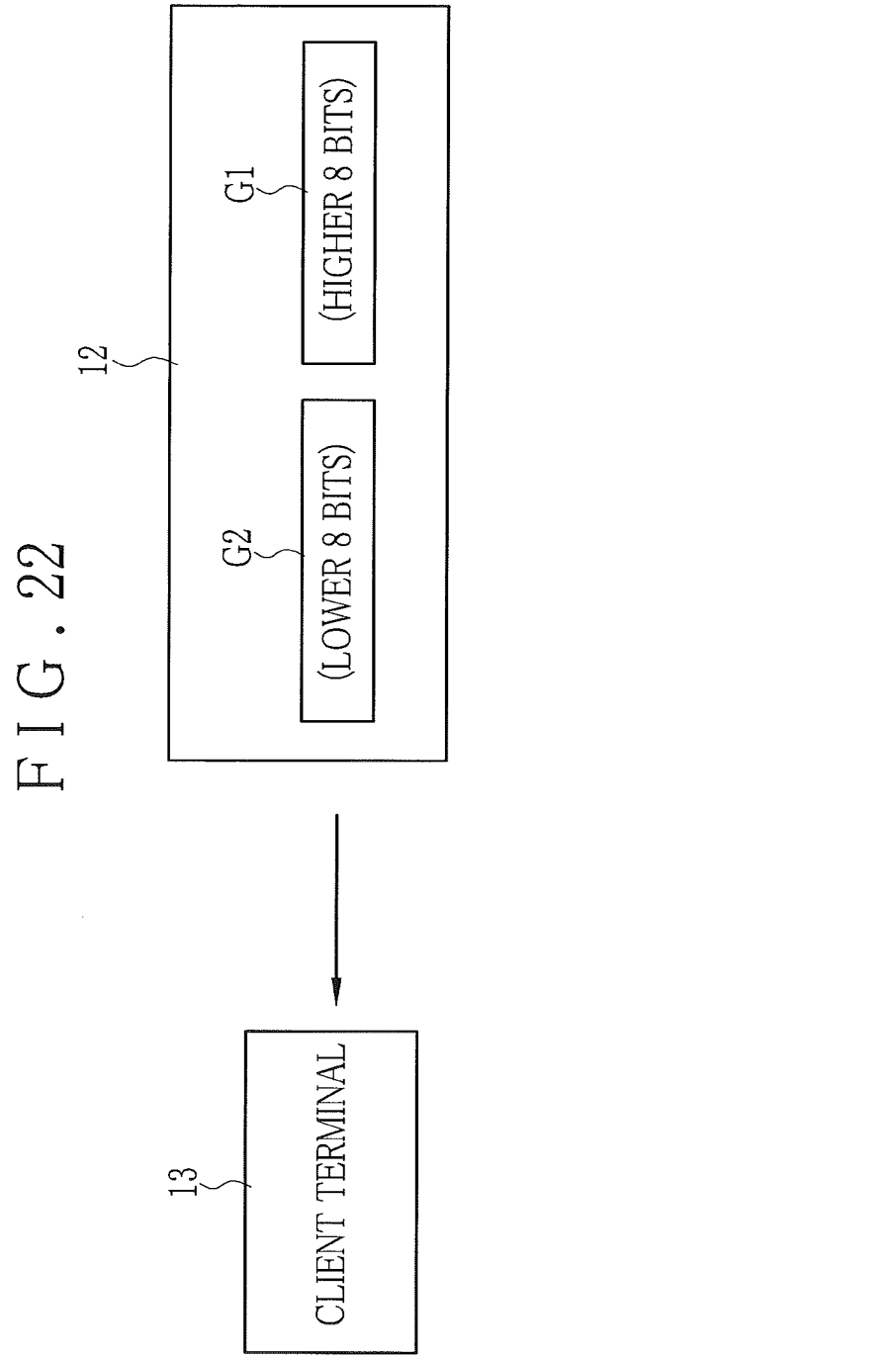

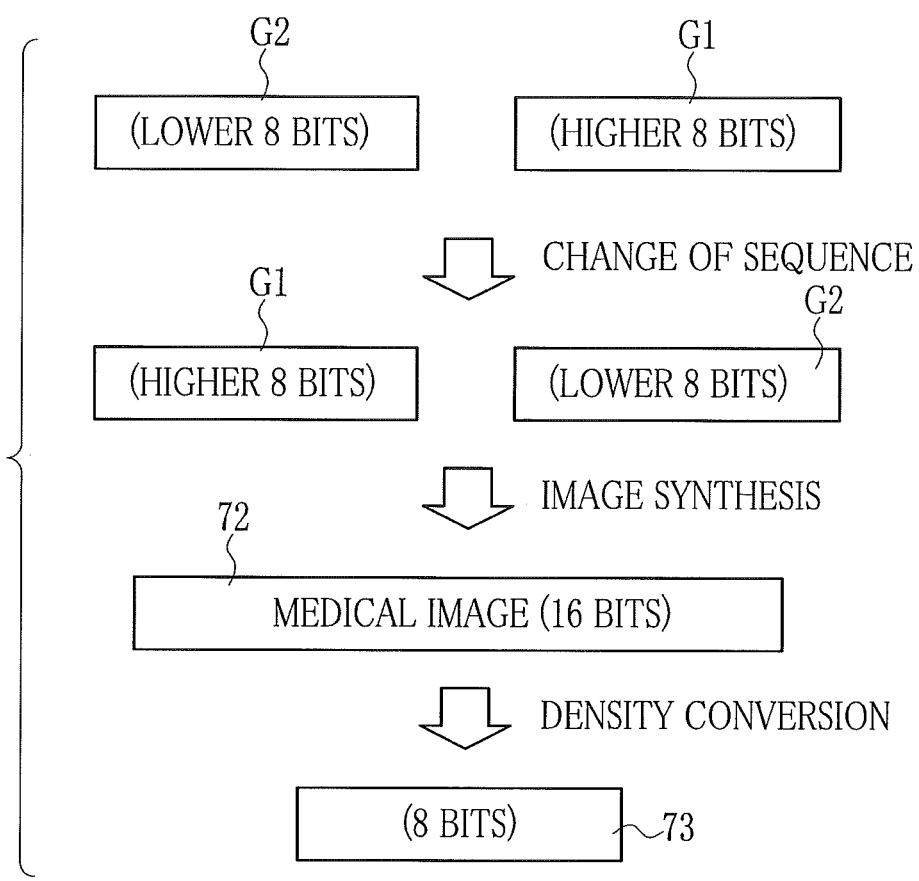

SYSTEM AND METHOD OF MANAGING MEDICAL IMAGE

CROSS-REFERENCE TO RELATED APPLICATION

This application is a Continuation of PCT International Application PCT/JP2013/074802 filed on 13 Sep. 2013, which claims priority under 35 USC 119(a) from Japanese Patent Application No. 2012-212592 filed on 26 Sep. 2012. The above application is hereby expressly incorporated by reference, in its entirety, into the present application.

BACKGROUND OF THE INVENTION

1. Field of the Invention

The present invention relates to a system and method of managing a medical image. More particularly, the present invention relates to a system and method of managing a medical image, in which the medical image after converting density can be rapidly displayed on a display surface of a client terminal.

2. Description Related to the Prior Art

A medical image managing system is widely used in a hospital or other medical facilities, for managing medical images in a form of electronic data, the medical images being formed by a modality unit such as a CR apparatus (computed radiography apparatus), DR apparatus (digital radiography apparatus), CT apparatus (computed tomography apparatus) or the like. The medical image managing system includes an image server and a client terminal. The image server stores the medical images formed by the modality unit. The client terminal is manipulated by a doctor or physician. The image server and the client terminal are connected to an internal network disposed in a hospital. The client terminal communicates with the image server through the internal network, so that the medical image filed in the image server is read out and displayed on a monitor.

In a medical facility, the use of a portable terminal apparatus as the client terminal in the medical image managing system has been increased, such as a PDA (personal digital assistant), smart phone (high performance mobile telephone), tablet and the like. The portable terminal apparatus is connected to a wireless LAN (wireless local area network) in the internal network, or to a telephone line of the mobile telephone, so that viewing of the medical image is possible in various places.

For diagnosis of the medical image, density conversion is performed to convert density of the medical image to enhance its high or low density portions for the purpose of facilitating the diagnosis according to a body part of the medical image or a modality of the modality unit. The medical image is stored in the image server in a format of a multi-level gradation image (high resolution image) with gradation of 9-16 bits per one pixel, or lossless JPEG image without degradation, The density conversion of the medical image is to determine a center value of the gradation and a width of the gradation about the center value for the medical image of the multi-level gradation, for converting the gradation of the medical image. The density conversion is generally referred to as window level conversion.

For example, the medical image managing system of JP-A 2012-100899 includes the image server and the client terminal. The image server processes the medical image in the density conversion. The client terminal causes a monitor to display a density-converted medical image after the density conversion in the image server. In the medical image managing system, it is possible for the client terminal readily to display the density-converted medical image on the monitor after readout from the image server.

The medical image managing system of JP-A 2000-293528 includes the image server and the client terminal. The image server transmits the medical image to the client terminal. The client terminal processes the medical image in the density conversion after reception from the image server, and causes a monitor to display the density-converted medical image. In the medical image managing system, the density conversion is performed in the client terminal. Should initial conversion of density be insufficient, the density conversion is performed again, so that processing time for the density conversion may be long. However, transmission of the medical image from the image server after the density conversion is unnecessary. So the total of the processing time can be shortened.

In general, it is necessary rapidly to display the density-converted medical image at the client terminal in the medical image managing system for medical diagnosis. However, displaying may be slower according to a condition of using the medical image managing system. For example, in the medical image managing system of JP-A 2012-100899, time for transmitting the medical image from the image server to the client terminal is longer assuming that a communication speed between the image server and the client terminal is low. Displaying the density-converted medical image at the client terminal becomes slow. Communication time of the medical image is changed because the communication speed changes according to a place of the communication in case the portable terminal apparatus is connected to the image server by the wireless LAN or the telephone line of the mobile telephone. Also, the communication time changes with dependency to a data size.

In the medical image managing system in JP-A 2000-293528, rapidity in displaying the density-converted medical image may be varied according to a structure of the system based on performance of the client terminal in use, a type of the software and the like. For example, should the portable terminal apparatus be an old type, displaying requires time because of a low level of the communication speed or a processing time of data. In case the portable terminal apparatus of a new type is used, displaying can be rapid owing to high performance.

Rapidity of displaying the density-converted medical image is influenced by a construction, a communication condition or the like of the medical image managing system. In relation to a first structure for density conversion in the image server and a second structure for density conversion in the client terminal, which of the first and second structures can display the density-converted medical image reliably earlier than the remainder cannot be determined. It is difficult to determine which of the two should be selected for the density conversion in an effective manner.

SUMMARY OF THE INVENTION

In view of the foregoing problems, an object of the present invention is to provide a system and method of managing a medical image, in which the medical image after converting density can be rapidly displayed on a display surface of a client terminal.

In order to achieve the above and other objects and advantages of this invention, a medical image managing system has an image server for managing a plurality of a medical image, and a client terminal, connected to the image server in a networked arrangement, for causing a monitor to display a density-converted medical image obtained by density conversion of the medical image. The medical image managing system includes a communication speed measurer for measuring a communication speed between the image server and the client terminal. A processing speed detector detects a processing speed of the client terminal for the density conversion. A density conversion mode checker compares processing time of a first density conversion mode and processing time of a second density conversion mode after acquisition according to the communication speed measured by the communication speed measurer, the processing speed of the client terminal detected by the processing speed detector, and a predetermined processing speed of the image server, so as to select one of the density conversion modes with a shorter value of the processing time. An image processor, upon selecting the first density conversion mode, transmits the density-converted medical image to the client terminal after the density conversion of the medical image in the image server, and upon selecting the second density conversion mode, transmits the medical image to the client terminal to perform the density conversion of the medical image in the client terminal.

Preferably, the density conversion mode checker acquires first density conversion time for the density conversion of the medical image in the image server, first communication time for transmitting the density-converted medical image from the image server to the client terminal, second communication time for transmitting the medical image from the image server to the client terminal, and second density conversion time for the density conversion of the medical image in the client terminal. The density conversion mode checker compares the first mode processing time obtained by adding up the first density conversion time and the first communication time with the second mode processing time obtained by adding up the second density conversion time and the second communication time.

Preferably, the processing speed detector measures the processing speed of the client terminal for the density conversion.

Preferably, the processing speed detector causes the client terminal to perform the density conversion of a measurement image, and measures the processing time according to a data size of the measurement image and time taken for the density conversion.

In another preferred embodiment, the processing speed detector detects the processing speed of the client terminal for the density conversion according to device-specific information of the client terminal transmitted from the client terminal to the image server.

Preferably, the communication speed measurer causes the image server and the client terminal to communicate with measurement data, and measures the communication speed according to a data size of the measurement data and time taken for communication of the measurement data.

Preferably, the image server includes an image decomposition processing device for decomposing the medical image into at least a higher bit image of higher order bits of gradation levels of the medical image and a lower bit image of lower order bits of the gradation levels of the medical image. In the second density conversion mode, the higher bit image and the lower bit image decomposed by the image decomposition processing device are transmitted to the client terminal.

Preferably, a bit number of the higher bit image and the lower bit image is equal to or less than an upper limit of a bit number processable in the client terminal as an image.

Preferably, the image server compresses a first one of the higher bit image and the lower bit image with larger influence to visual recognition of the medical image in lossless compression, and compresses a remaining one of the higher bit image and the lower bit image in lossy compression, before transmission of the higher bit image and the lower bit image to the client terminal.

Preferably, the client terminal reconstructs the medical image by synthesizing the higher bit image and the lower bit image, and performs the density conversion of the medical image being reconstructed.

Preferably, the image server transmits the lower bit image to the client terminal before transmitting the higher bit image to the client terminal. The client terminal changes a sequence of the lower bit image and the higher bit image before synthesizing the higher bit image with the lower bit image.

Also, a medical image managing method for a medical image managing system is provided, the medical image managing system having an image server for managing a plurality of a medical image, and a client terminal, connected to the image server in a networked arrangement, for causing a monitor to display a density-converted medical image obtained by density conversion of the medical image. The medical image managing method includes a step of measuring a communication speed between the image server and the client terminal. A processing speed of the client terminal for the density conversion is detected. Processing time of a first density conversion mode and processing time of a second density conversion mode are compared after acquisition according to the communication speed, the processing speed of the client terminal, and a predetermined processing speed of the image server, so as to select one of the density conversion modes with a shorter value of the processing time. Upon selecting the first density conversion mode, the density-converted medical image is transmitted to the client terminal after the density conversion of the medical image in the image server. Upon selecting the second density conversion mode, the medical image is transmitted to the client terminal to perform the density conversion of the medical image in the client terminal.

Consequently, the medical image after converting density can be rapidly displayed on a display surface of a client terminal, because the values of the processing time of first and second density conversion modes are compared to minimize the total of the processing time.

BRIEF DESCRIPTION OF THE DRAWINGS

The above objects and advantages of the present invention will become more apparent from the following detailed description when read in connection with the accompanying drawings, in which:

FIG. 7 is an explanatory view illustrating a structure of measurement data;

FIG. 8 is a table illustrating an example of a communication speed and processing speed for use in detecting the density conversion modes;

FIG. 16 is a table illustrating an example of a processing speed database of the second embodiment;

FIG. 22 is a schematic view illustrating steps of transmitting decomposed images in the fourth embodiment;

FIG. 23 is a schematic view illustrating steps of density conversion of the decomposed images.

DETAILED DESCRIPTION OF THE PREFERRED EMBODIMENT(S) OF THE PRESENT INVENTION

First Embodiment

Figure 1:
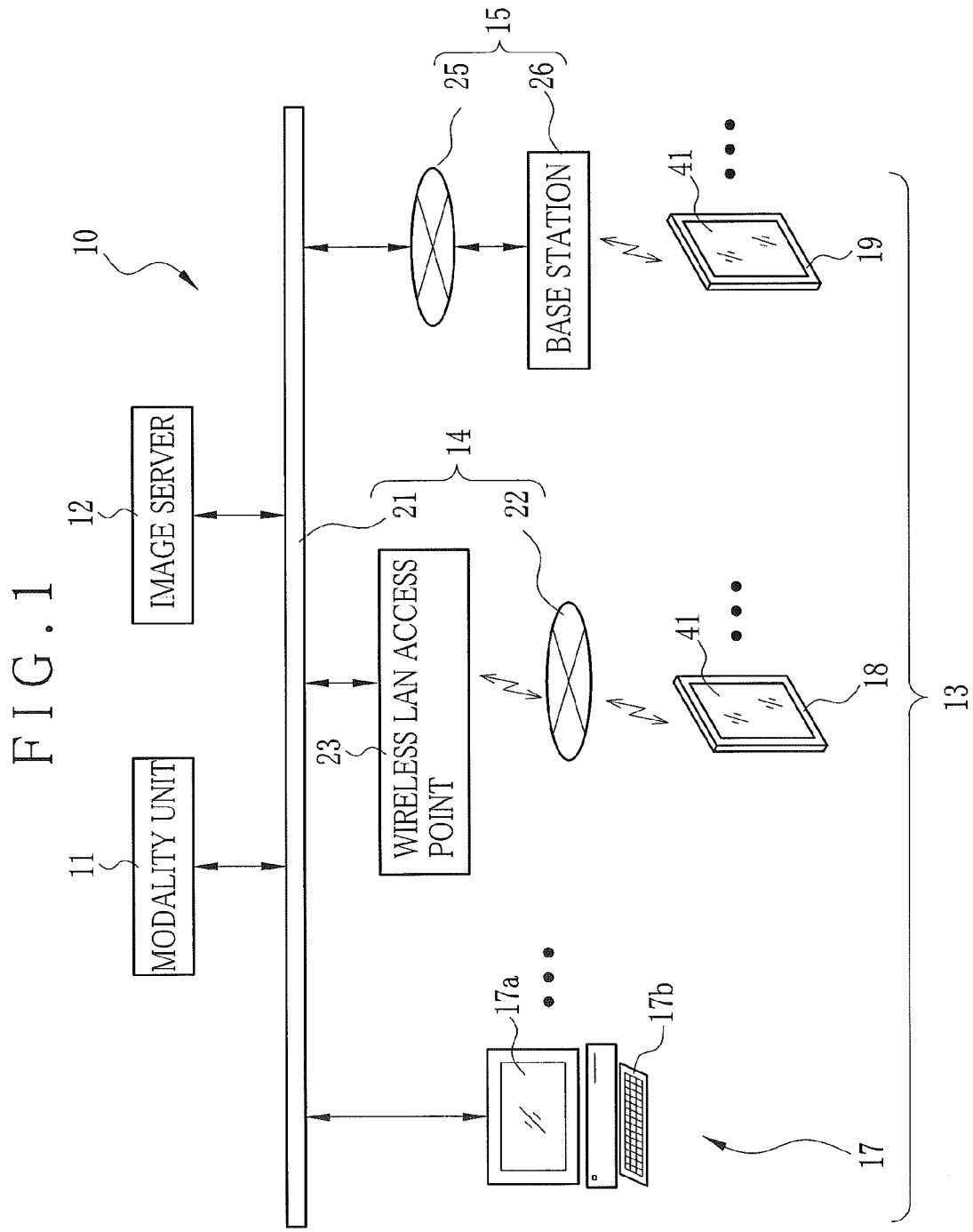
FIG. 1 is a schematic view illustrating an example of a medical image managing system.

In FIG. 1, a medical image managing system 10 includes a modality unit 11, an image server 12 (server apparatus), plural client terminals 13 (terminal apparatuses), an internal network 14 and an external network 15. The image server 12 manages medical images formed by the modality unit 11. The client terminals 13 read out the medical images from the image server 12 for viewing. The internal network 14 and the external network 15 connect those elements in a communicable manner. The client terminals 13 include an installed type of plural image diagnosis apparatuses 17, and plural portable terminal apparatuses 18 and 19. The image diagnosis apparatuses 17 are connected to the internal network 14 in a wired manner. The portable terminal apparatuses 18 are connected to the internal network 14 in a wireless manner. The portable terminal apparatuses 19 are connected to the external network 15 through a telephone line of the mobile telephone. The medical image managing system 10 is established in a medical facility such as a hospital, clinic or the like.

The internal network 14 is a network disposed in the medical facility, and includes a wired LAN 21 and a wireless LAN 22. LAN cables (not shown) connect the modality unit 11, the image server 12 and the image diagnosis apparatuses 17 to the wired LAN 21. A wireless LAN access point 23 (access point device) is connected to the wired LAN 21, to establish the wireless LAN 22. A plurality of the portable terminal apparatuses 18 are connected to the wireless LAN 22 wirelessly. In FIG. 1, only one wireless LAN access point 23 is illustrated. However, a plurality of wireless LAN access points 23 are disposed to cover communication within a predetermined area in a building of the medical facility. It is possible with the portable terminal apparatuses 18 to view medical images in various places in the medical facility.

The external network 15 is a network disposed outside the medical facility, and is constituted by an IP network 25 (Internet protocol network) and a base station 26 of a mobile service provider. The IP network 25 is connected with the internal network 14. The base station 26 is connected with the IP network 25. A plurality of the portable terminal apparatuses 19 are connected to the base station 26 by the telephone line of the mobile telephone. In FIG. 1, only one base station 26 is illustrated. However, a plurality of base stations 26 are disposed to cover communication of the portable terminal apparatuses 19 within a predetermined area. It is possible to view a medical image with the portable terminal apparatuses 19 in various places outside the medical facility.

Examples of the modality unit 11 are a CR apparatus, DR apparatus and the like. The CR apparatus (computed radiography apparatus) forms an X-ray image by use of an imaging plate having a coating of photostimulable phosphor, and scans the imaging plate with a laser beam after imaging, to read an X-ray image on the imaging plate as electronic data. The DR apparatus (digital radiography apparatus) forms an X-ray image by use of a flat panel detector (FPD) where pixels are arranged in a matrix form for storing signal charge according to an incident dose of X-rays, and detects the X-ray image as electronic data by converting the signal charge stored by the pixels into a voltage signal in a signal processing circuit. The medical image formed by the modality unit 11 is transmitted to the image server 12 through the wired LAN 21. At this time, the modality unit 11 writes a patient ID and the like to an area of the medical image as metadata, so that the medical image can be searched in the image server 12.

An example of the image server 12 is a server of the PACS (Picture Archiving and Communication System). The image server 12 is constituted by a personal computer (PC), and includes a CPU, storage, memory, input device and monitor display panel. The storage stores a control program and an application program. The memory is a working memory with which the CPU performs tasks. The input device includes a mouse, keyboard and the like.

Each of the image diagnosis apparatuses 17 is a personal computer (PC) of a desktop type or notebook type, in which an image viewer as a program for viewing medical images is installed. The image diagnosis apparatuses 17 include a monitor 17a (display device) and an input device 17b (user input interface), which has a mouse, keyboard and the like. A plurality of the image diagnosis apparatuses 17 are disposed, for example, in each of hospital rooms of consultation, or for each of hospital departments, and manipulated by a doctor, nurse or the like. The image diagnosis apparatuses 17 perform login to the image server 12, read out a medical image from the image server 12, and cause the monitor 17a to display a density-converted medical image.

The portable terminal apparatuses 18 and 19 are a PDA, smart phone or tablet terminal in which the same image viewer as the image diagnosis apparatuses 17 is installed. A touchscreen panel 41 (user input interface and display device) is incorporated in the portable terminal apparatuses 18 and 19 for displaying a medical image and manipulation of the portable terminal apparatuses 18 and 19. A plurality of the portable terminal apparatuses 18 and 19 are disposed, for example, in each of hospital rooms of consultation, or for each of hospital departments. Also, one portable terminal apparatus 18 or 19 may be assigned to each one of doctors or nurses. The portable terminal apparatuses 18 and 19 log in to the image server 12 through the internal network 14 or the external network 15, reads out a medical image from the image server 12, and causes the touchscreen panel 41 to display a density-converted medical image.

Figure 2:
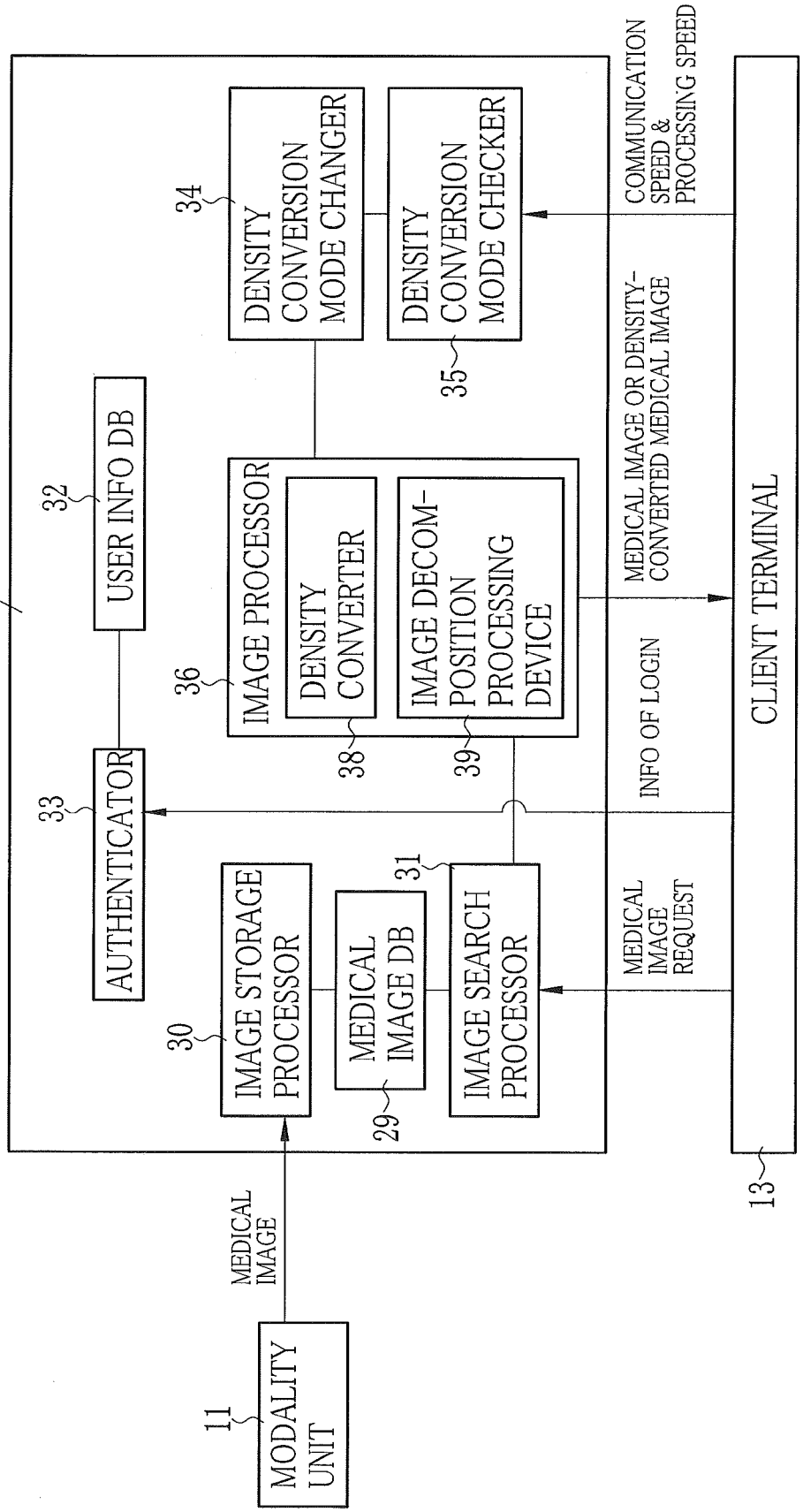
FIG. 2 is a block diagram schematically illustrating functional arrangement of an image server.

In FIG. 2, an image server program as an application program is stored in storage of the image server 12 for functioning the PC as an image server. In case the image server program is run in the image server 12, a CPU in the image server 12 functions as illustrated in FIG. 2 by way of a medical image database 29 (storage medium), an image storage processor 30, an image search processor 31, a user information database 32 (storage medium), an authenticator 33, a density conversion mode changer 34, a density conversion mode checker 35 and an image processor 36.

The medical image database 29 stores medical images obtained by the modality unit 11. Examples of the medical images are a multi-level gradation image (high resolution image) with gradation of 9-16 bits per one pixel, or lossless JPEG image without degradation, and are stored in the medical image database 29 in a file format according to the DICOM (Digital Imaging and Communications in Medicine). The image storage processor 30 writes the medical images to the medical image database 29 for storing. The image search processor 31 searches and reads out a medical image from the medical image database 29 according to a medical image request transmitted from the client terminal 13.

The user information database 32 stores information related to a user performing login from the client terminal 13 to the image server 12. The user in the present embodiment is a doctor or physician, nurse, or other medical service provider working in the medical facility. Examples of the user information are attribute information of the user, a user ID and password for the login, and the like. Examples of the attribute information are a name of a user, a medical qualification of a doctor, nurse or the like, a workplace, and the like.

The authenticator 33 performs authentication to check whether readout of a medical image should be allowed or not upon login of the client terminal 13 to the image server 12 for reading out the medical image. The authentication is performed by comparing the user ID and password transmitted from the client terminal 13 and those stored in the user information database 32. Assuming that the user information database 32 stores a user ID and password coinciding with those being transmitted, then the authenticator 33 authenticates the client terminal 13. Assuming that the user information database 32 does not store a user ID and password coinciding with those being transmitted, then the client terminal 13 is not authenticated.

The density conversion mode changer 34 changes over a density conversion mode for density conversion of a medical image. In diagnosis according to the medical image, the density conversion is performed to convert density of the medical image to enhance portions of high and low densities in the medical image (namely, contrast enhancement) to facilitate the diagnosis of the medical image according to a body part or a type of the modality unit having formed the medical image. The density conversion mode in the medical image managing system 10 of the present embodiment is first and second density conversion modes.

In the first density conversion mode, the image processor 36 in the image server 12 processes a medical image in the density conversion, to generate a density-converted medical image, which is transmitted from the image server 12 to the client terminal 13. In the second density conversion mode, the image processor 36 transmits a medical image to the client terminal 13, where an image processor 48 (See FIG. 3) processes the medical image in the density conversion, to generate a density-converted medical image.

The density conversion mode checker 35 checks which of first and second density conversion modes should be used for performing the density conversion of the medical image. Specifically, the density conversion mode checker 35 calculates processing time in use of the first density conversion mode and processing time in use of the second density conversion mode, compares values of those, and determines one of the density conversion modes with shorter processing time, namely one for rapidly displaying a density-converted medical image at the client terminal 13. The density conversion mode changer 34 changes over the density conversion mode according to a detection result of the density conversion mode checker 35.

The image processor 36 includes a density converter 38 (for contrast enhancement) and an image decomposition processing device 39. Upon changing over the density conversion mode to the first density conversion mode, the density converter 38 processes the medical image read out from the medical image database 29 in the density conversion. Upon changing over the density conversion mode to the second density conversion mode, the image decomposition processing device 39 decomposes the medical image read out from the medical image database 29 into at least a higher bit image and a lower bit image for transmission to the client terminal 13 for the client terminal 13 to treat the medical image.

Figure 3:
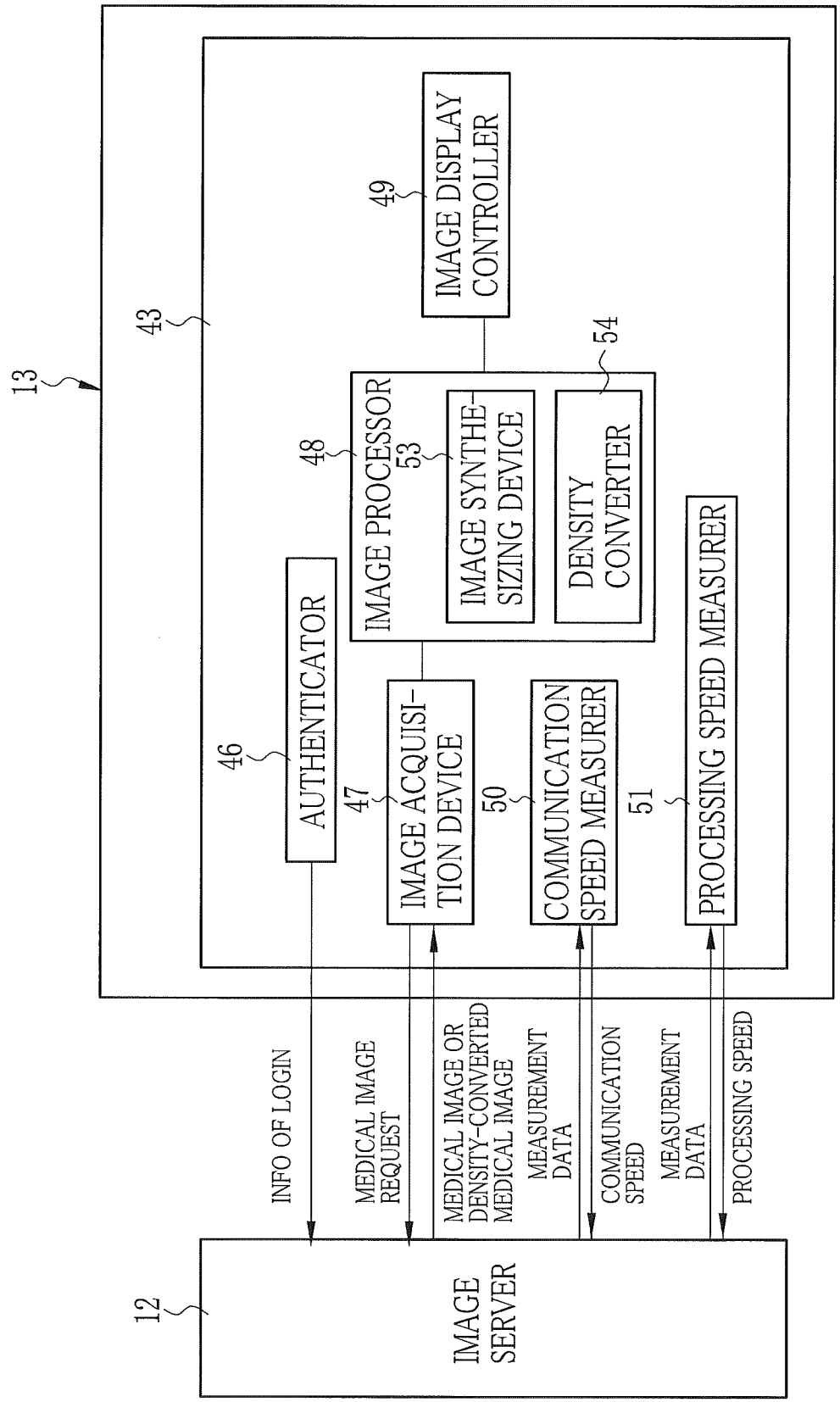
FIG. 3 is a block diagram schematically illustrating functional arrangement of a client terminal.

An image viewer of the client terminal 13 is described next. In FIG. 3, a browser 43 is started up by running the image viewer in the client terminal 13. The browser 43 is a web browser of a known type for connection to the Internet. The image viewer is a web application executable with the browser 43. The browser 43 functions as an authenticator 46, an image acquisition device 47, the image processor 48, an image display controller 49, a communication speed measurer 50 and a processing speed measurer 51 which constitute the image viewer.

The authenticator 46 performs authentication for the image server 12 at the time of reading out medical images from the image server 12 through the client terminal 13. In the authentication, the authenticator 46 causes the monitor 17a of the image diagnosis apparatus 17 or the touchscreen panel 41 of the portable terminal apparatus 18 or 19 to display an input menu for a user ID and a password for login. Upon inputting the user ID and the password from a user, the authenticator 46 transmits information of the login and the user ID and the password to the image server 12. The authenticator 33 in the image server 12 performs the authentication, by use of the user ID and the password. Upon authenticating the client terminal 13 in the image server 12, the client terminal 13 is enabled to read out a medical image from the image server 12.

The image acquisition device 47 reads out a medical image from the image server 12. In case there is an input at the browser 43 for reading out the medical image, the image acquisition device 47 transmits a medical image request to the image server 12 for requesting readout of the medical image. The medical image request includes request information, for example, a patient ID specified by a user, and the like. Also, the image acquisition device 47 receives the medical image or density-converted medical image from the image server 12.

The image processor 48 includes an image synthesizing device 53 and a density converter 54 (for contrast enhancement). In case the density conversion mode is changed over to the second density conversion mode, the image synthesizing device 53 synthesizes a higher bit image and a lower bit image transmitted from the image server 12, to reconstruct the original medical image. The density converter 54 processes the medical image synthesized by the image synthesizing device 53 for the density conversion.

The image display controller 49 causes the monitor 17a of the image diagnosis apparatus 17 or the touchscreen panel 41 of the portable terminal apparatus 18 or 19 to display a density-converted medical image transmitted from the image server 12, or a density-converted medical image after the density conversion in the image processor 48.

The communication speed measurer 50 measures a communication speed between the image server 12 and the client terminal 13. An example of the communication speed is the number of bits of communication per one second (bps). The communication speed measured by the communication speed measurer 50 is used in the density conversion mode checker 35 of the image server 12 to check a density conversion mode.

The processing speed measurer 51 (corresponding to a processing speed detector) measures a processing speed of the density conversion of a medical image in the image processor 36. An example of the processing speed is the number of bits of processing per one second (bps). The processing speed measured by the processing speed measurer 51 is used for detecting a density conversion mode in the density conversion mode checker 35, in a manner similar to the communication speed measured by the communication speed measurer 50.

Figure 4:
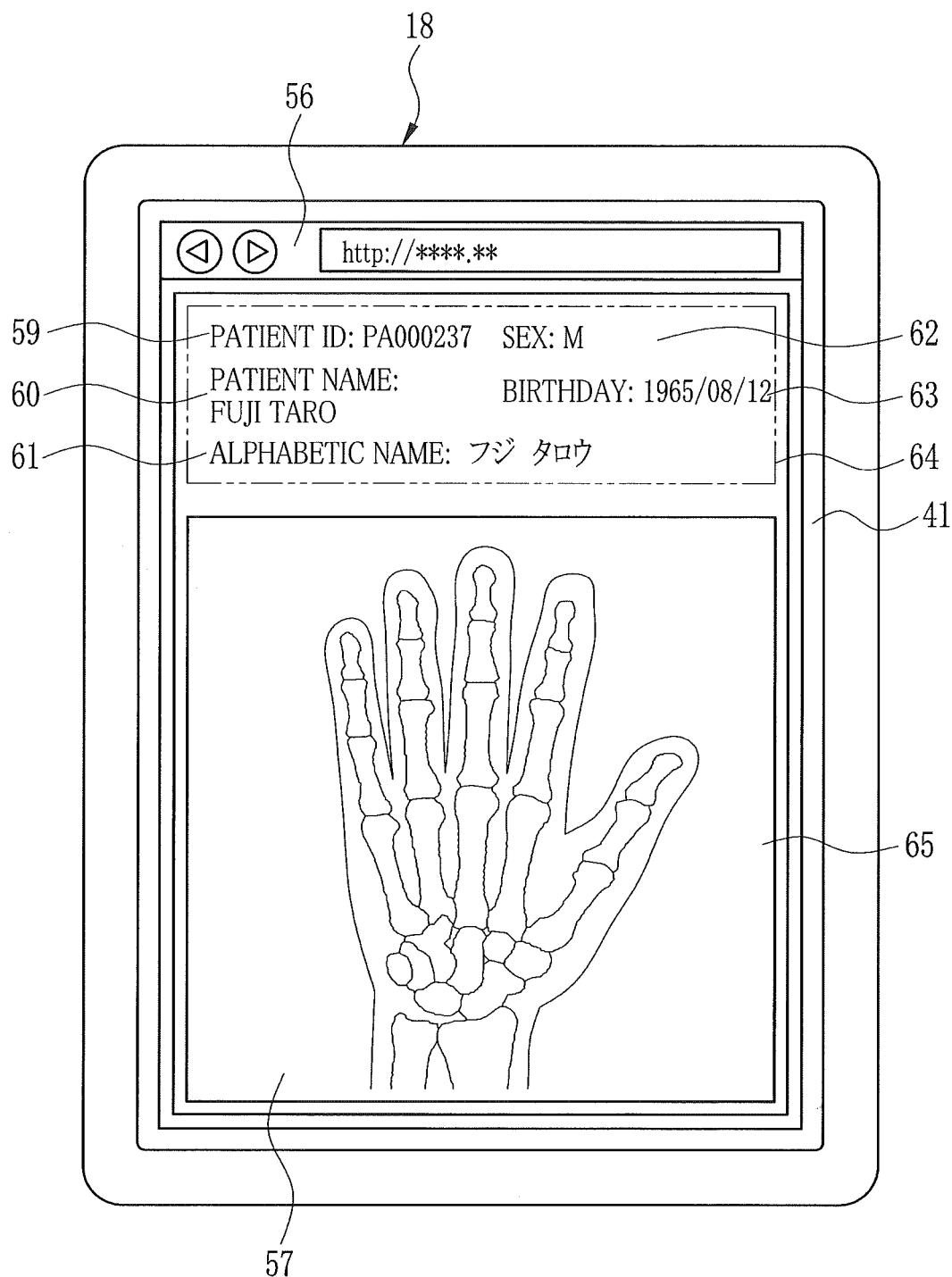
FIG. 4 is an explanatory view illustrating an example of a displayed medical image on a portable terminal apparatus.

In FIG. 4, the image display controller 49, for example, causes a medical image screen area 57 to appear in a browser screen area 56 of the browser 43 displayed on the touchscreen panel 41 of the portable terminal apparatuses 18. A patient information display field 64 is an upper portion of the medical image screen area 57, and includes a patient ID field 59, a patient name field 60, an alphabetic name field 61 with kana characters, a sex field 62 and a birthday field 63. An image display field 65 is disposed lower than the patient information display field 64 to display a medical image of the patient. Note that the browser screen area 56 and the medical image screen area 57 are also displayed in the image diagnosis apparatuses 17 and the portable terminal apparatuses 19, but are not described further, because the same as those of the portable terminal apparatuses 18.

Detection of a density conversion mode, changeover of the density conversion mode and the density conversion are described next by referring to FIGS. 5 and 6. In case a medical image request is transmitted by the image acquisition device 47 of the client terminal 13 (for example, the portable terminal apparatus 18) in the step S1, the image server 12 transmits measurement data to the client terminal 13 in the step S2. In FIG. 7, measurement data 68 (test data) is constituted by a start time point BT and a measurement image 68a (test image) of a small data size. At the start time point BT, transmission of the measurement data 68 is started from the image server 12 to the client terminal 13. The measurement data 68 is used for measuring the communication speed and processing speed in the communication speed measurer 50 and the processing speed measurer 51.

The communication speed measurer 50 measures a reception time point RT of receiving the measurement data 68, subtracts the start time point BT of the transmission of the measurement data 68 from the reception time point RT, and obtains communication time CT taken for communication of the measurement data 68. Then the communication speed measurer 50 divides a data size Md of the measurement data 68 by the communication time CT of the measurement data 68 in a manner of Md/CT, to obtain a communication speed CS between the image server 12 and the client terminal 13 in the step S3.

The processing speed measurer 51 causes the density converter 54 of the image processor 48 to process the measurement image 68a of the measurement data 68 in the density conversion, and measures processing time PT required for the density conversion. The processing speed measurer 51 divides a data size Mp of the measurement image by the processing time PT in a manner of Mp/PT, to determine a processing speed PS of the density converter 54 in the step S4.

The communication speed CS and processing speed PS measured by the communication speed measurer 50 and the processing speed measurer 51 are transmitted from the client terminal 13 to the image server 12 in the step S5. The processing times of the first and second density conversion modes are obtained from the measured speeds and the processing speed of the image server 12, before a shorter one of the values of the processing times is selected by comparison in the step S6. The processing speed of the image server 12 has been measured previously, and stored in a memory as predetermined data.

Figure 6:
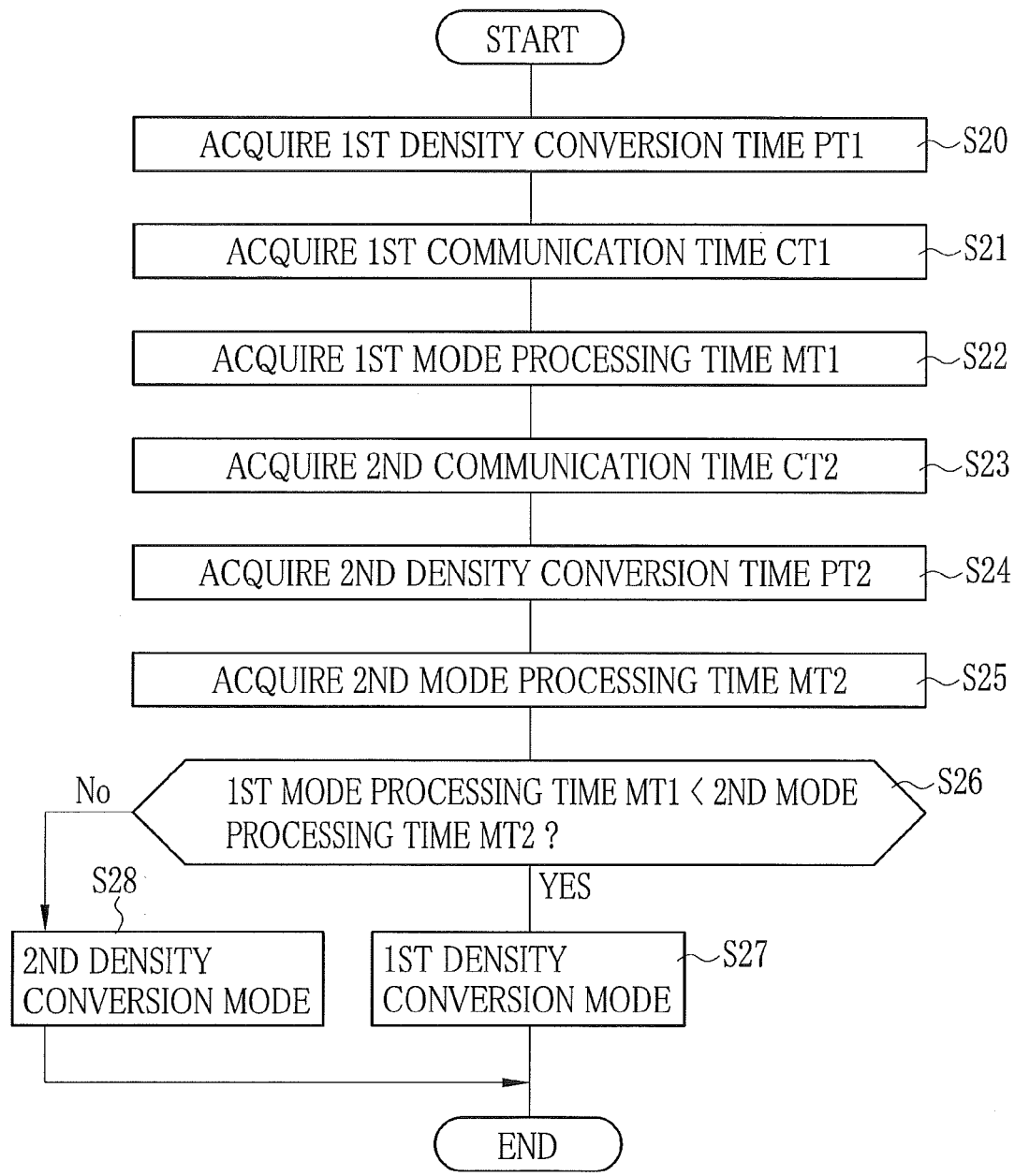
FIG. 6 is a flow chart illustrating details of steps of the density conversion modes.

Acquisition of the processing times of the first and second density conversion modes is performed in steps of FIG. 6 in the density conversion mode checker 35 of the image server 12. For the first density conversion mode, at first the density conversion mode checker 35 determines first density conversion time PT1 in the step S20 for density conversion of a request image (particular medical image) requested by the client terminal 13 by use of the density converter 38 of the image server 12. The first density conversion time PT1 is obtained by dividing a data size M1 of the request image by a processing speed PS3 of the density converter 38 in a manner of M1/PS3. Then the density conversion mode checker 35 determines first communication time CT1 in the step S21 for transmitting a density-converted medical image after the density conversion in the image server 12 to the client terminal 13, according to the communication speed CS. The first communication time CT1 is obtained by dividing a data size M2 of a density-converted medical image by the processing speed CS in a manner of M2/CS. The density conversion mode checker 35 adds up the first density conversion time PT1 and the first communication time CT1, to obtain the first mode processing time MT1 for the density conversion mode in the step S22.

Note that the data size M2 is an estimated data size as a result of the density conversion by evaluating data of the request image having the data size M1.

For the second density conversion mode, the density conversion mode checker 35 determines second communication time CT2 in the step S23 for transmitting a request image (particular medical image) from the image server 12 to the client terminal according to the communication speed CS. The second communication speed CT2 is obtained by dividing the data size M1 of the request image by the communication speed CS in a manner of M1/CS. Then the density conversion mode checker 35 determines second density conversion time PT2 in the step S24 for the density conversion of the request image in the density converter 54 of the client terminal 13 according to the processing speed PS of the client terminal 13. The second density conversion time PT2 is obtained by dividing the data size M1 of the request image by the processing speed PS of the density converter 54 in a manner of M1/PS. The density conversion mode checker 35 adds up the second density conversion time PT2 and the second communication time CT2, to obtain the second mode processing time MT2 for the density conversion mode in the step S25.

The density conversion mode checker 35 compares the first mode processing time MT1 with the second mode processing time MT2 in the step S26. Assuming that the first mode processing time MT1 is shorter than the second mode processing time MT2 (yes in the step S26), the density conversion mode checker 35 selects the first density conversion mode in the step S27. Assuming that the second mode processing time MT2 is equal to or shorter than the first mode processing time MT1 (no in the step S26), the density conversion mode checker 35 selects the second density conversion mode in the step S28.

Symbols representing the communication speed and processing speed of the various devices are indicated in a table 70 of FIG. 8. Specifically, the table 70 has information of a communication speed CS1 between the image server 12 and the image diagnosis apparatus 17, a communication speed CS2 between the image server 12 and the portable terminal apparatus 18 connected to the wireless LAN 22, a communication speed CS3 between the image server 12 and the portable terminal apparatus 19 connected to the mobile telephone line, a processing speed PS1 of the image diagnosis apparatus 17, a processing speed PS2 of the portable terminal apparatuses 18 and 19, and the processing speed PS3 of the image server 12. Note that the processing speed PS3 of the image server 12 has been already predetermined, and is not measured at the time of selecting a density conversion mode.

For the image interpretation of medical images in the image diagnosis apparatus 17, the first and second mode processing times MT1 and MT2 are obtained according to the communication speed CS1 between the image server 12 and the image diagnosis apparatus 17, the processing speed PS1 of the image diagnosis apparatus 17, and the processing speed PS3 of the image server 12.

The wired LAN 21 performs connection between the image server 12 and the image diagnosis apparatus 17, so that the communication speed CS1 is high for a stabilized state of the communication. Each of the image server 12 and the image diagnosis apparatus 17 are a personal computer (PC) of a desktop type, so that there is no large difference between the processing speeds PS1 and PS3. In this situation, selection of the first density conversion mode from the first and second density conversion modes is more frequent. This is because the processing time in the first density conversion mode for transmitting a density-converted medical image with a small data size from the image server 12 to the client terminal 13 is shorter than the processing time in the second density conversion mode for transmitting a medical image with a large data size from the image server 12 to the client terminal 13. Note that in case performance of processing in the image server 12 is lowered for a certain reason, or in case the communication speed of the wired LAN 21 is lowered, or in case the client terminal 13 has high performance, then the second density conversion mode is selected, because the speed can be set higher by the density conversion in the client terminal 13.

For the image interpretation of a medical image in the portable terminal apparatus 18 connected to the wireless LAN 22, the first and second mode processing times MT1 and MT2 are obtained according to the communication speed CS2 between the image server 12 and the portable terminal apparatus 18, the processing speed PS2 of the portable terminal apparatus 18, and the processing speed PS3 of the image server 12.

As the image server 12 and the portable terminal apparatus 18 are interconnected by the wireless LAN 22, the processing speed CS2 is comparatively high. However, a communication state is more unstable than the wired LAN 21. Also, the processing speed PS2 of the portable terminal apparatus 18 is slightly smaller than that of the image server 12 which is the personal computer of the desktop type. While the communication state of the wireless LAN 22 is stable, the first density conversion mode is selected in a manner similar to the wired LAN 21. Assuming that the communication state of the wireless LAN 22 becomes unstable to lower the communication speed, the second density conversion mode is selected.

For the image interpretation of a medical image in the portable terminal apparatus 19 connected to the telephone line of the mobile telephone, the first and second mode processing times MT1 and MT2 are obtained according to the communication speed CS3 between the image server 12 and the portable terminal apparatus 19, the processing speed PS2 of the portable terminal apparatus 19, and the processing speed PS3 of the image server 12. As the image server 12 is connected with the portable terminal apparatus 19 by the telephone line of the mobile telephone, the communication speed CS3 is much lower than that of the wired LAN 21 or the wireless LAN 22, so that the communication state is more unstable than the wired LAN 21. Thus, the processing time in the second density conversion mode of density conversion in the client terminal 13 is shorter than in the first density conversion mode. The second density conversion mode is selected more frequently.

Figure 9:
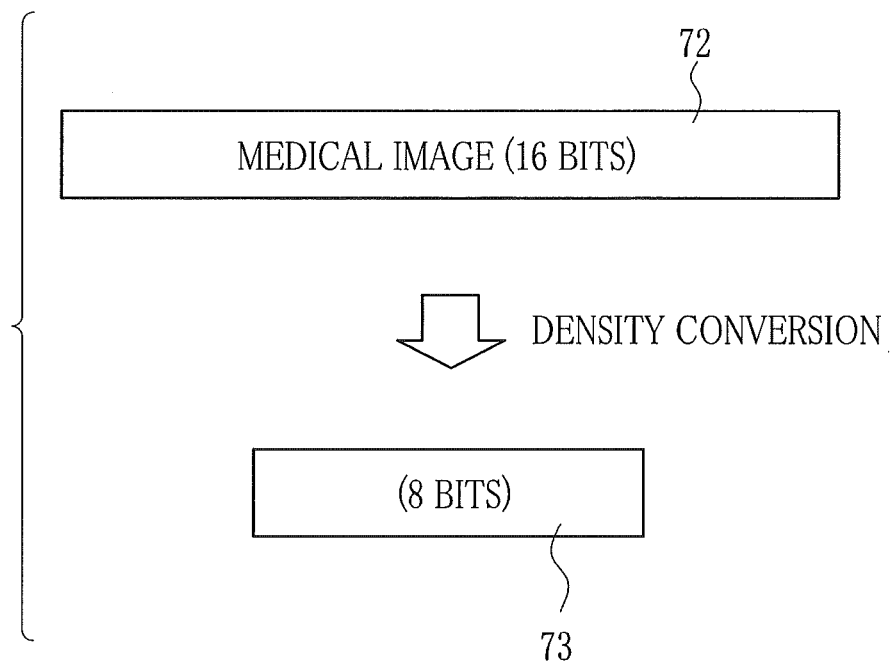
FIG. 9 is a schematic view illustrating steps of the density conversion.

In case the first density conversion mode is selected in the density conversion mode checker 35, the density conversion mode changer 34 changes over the density conversion mode to the first density conversion mode in the step S6. In the first density conversion mode, the density converter 38 of the image server 12 performs density conversion of a medical image in the step S7. In the density conversion, a center value of the gradation after the density conversion and a width of the gradation about the center value (for example, 8 bits) are determined from the medical image having the gradation levels of 16 bits read out from the medical image database 29. Image processing is performed for the medical image to become an image having the width of gradation corresponding to the determined center value. In FIG. 9, a density-converted medical image 73 having the gradation levels of 8 bits is formed from a medical image 72 having the gradation levels of 16 bits. Note that the center value and the width of the gradation after the density conversion can be set by the user as desired, or can be predetermined according to a body part to be imaged or a modality of the modality unit.

The density-converted medical image from the density converter 38 is transmitted from the image server 12 to the client terminal 13 in the step S8. The density-converted medical image in the client terminal 13 is caused by the image display controller 49 to appear in the image display field 65 of the medical image screen area 57 in FIG. 4 in the step S9.

In case the second density conversion mode is selected by the density conversion mode checker 35, the density conversion mode changer 34 changes over the density conversion mode to the second density conversion mode in the step S6. The image decomposition processing device 39 in the image server 12 decomposes the medical image into at least two in the step S10, and transmits those to the client terminal 13 in the step S11. The medical image is a gradation image with gradation levels of 9-16 bits per one pixel. In contrast with this, the client terminal 13 uses an image viewer operating on the browser 43 in use of the HTML language, and can treat only images of gradation levels of at most 8 bits per one pixel. Images of gradation levels of more than 8 bits cannot be recognized as images. Thus, the medical image is decomposed in the second density conversion mode in a form processable in the browser 43, and then transmitted to the client terminal 13.

Assuming that the bit number of a medical image is 8 bits or less, then the image server 12 can transmit the medical image to the client terminal 13 at one time.

Figure 10:
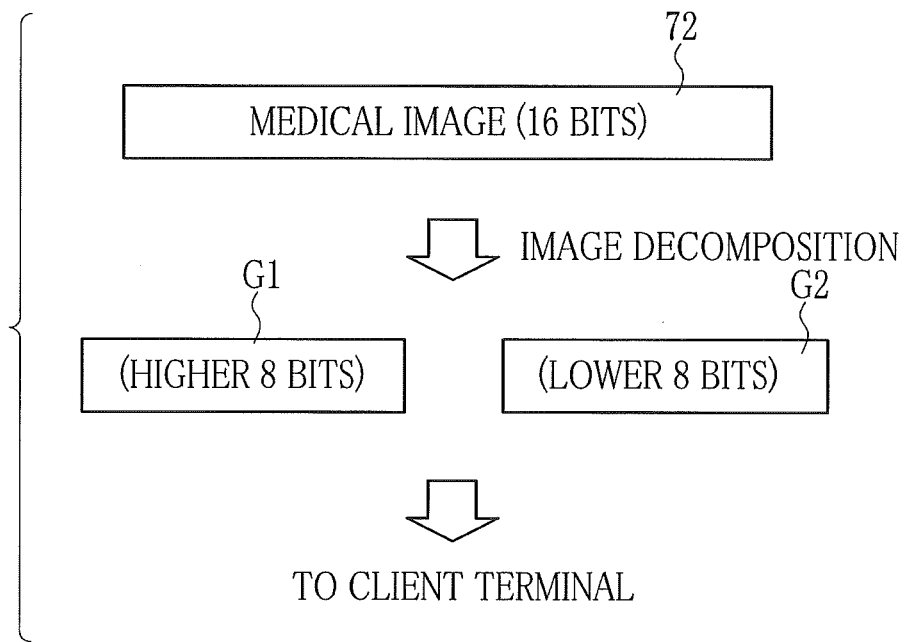
FIG. 10 is a schematic view illustrating steps of image decomposition.

In FIG. 10, the image decomposition processing device 39 decomposes the medical image 72 read out of the medical image database 29 into a higher bit image G1 and a lower bit image G2 in a condition under an upper limit of a bit number processable in the browser 43 of the client terminal 13. An example of the medical image 72 has 16 bits for the number of gradation levels. An example of the higher bit image G1 has 8 higher order bits of the gradation levels (8 higher bit planes). An example of the lower bit image G2 has 8 lower order bits of the gradation levels (8 lower bit planes). The image server 12 transmits the higher bit image G1 to the client terminal 13 in the step S11, and then transmits the lower bit image G2 to the client terminal 13 in the step S12.

Figure 11:
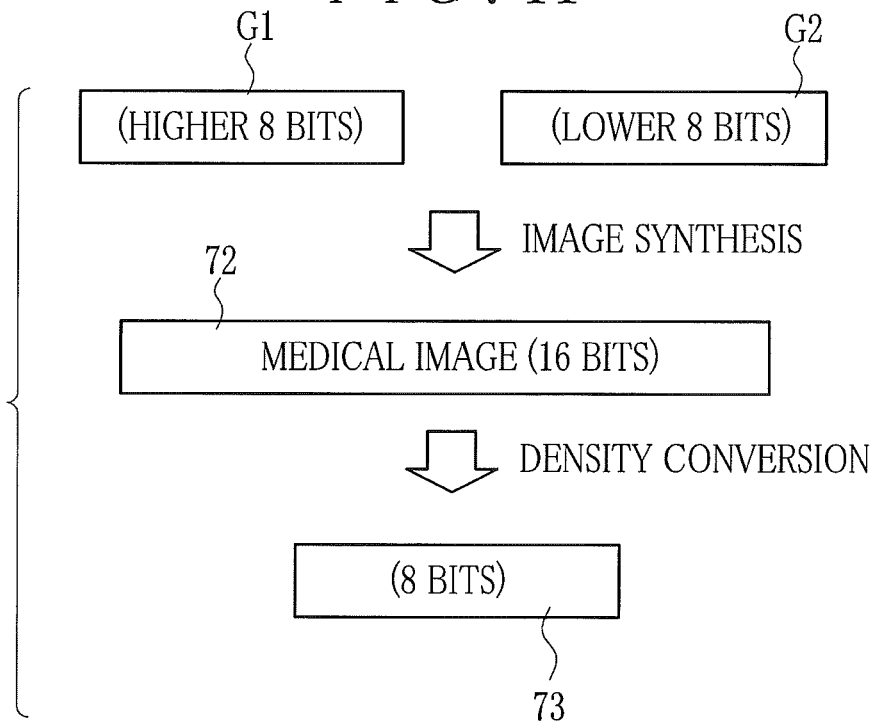
FIG. 11 is a schematic view illustrating steps of the density conversion of decomposed images.

In FIG. 11, the client terminal 13 upon receiving the higher bit image G1 and the lower bit image G2 from the image server 12 synthesizes the higher bit image G1 and the lower bit image G2 in the image synthesizing device 53 of the image processor 48, to reconstruct the medical image 72 in the step S13. The density converter 54 in the client terminal 13 processes the medical image in the density conversion, to generate a density-converted medical image in the step S14. The density conversion is the same processing as the density conversion in the image server 12. The image display controller 49 in the client terminal 13 causes the image display field 65 of the medical image screen area 57 of FIG. 4 to display the density-converted medical image from the density converter 54 in the step S9.

Figure 5:
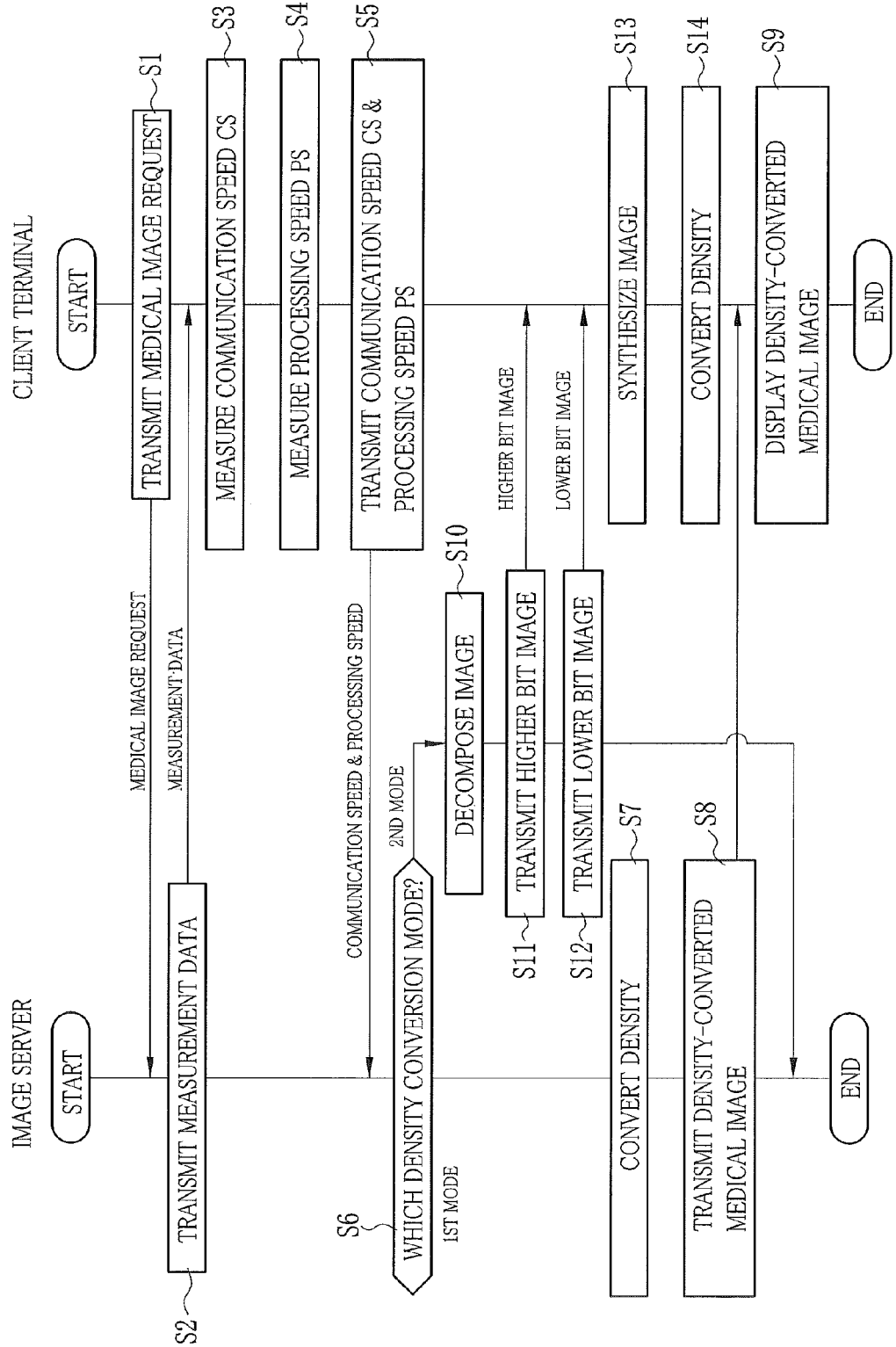
FIG. 5 is a flow chart illustrating detection of density conversion modes and steps of the density conversion modes.
Figure 12:
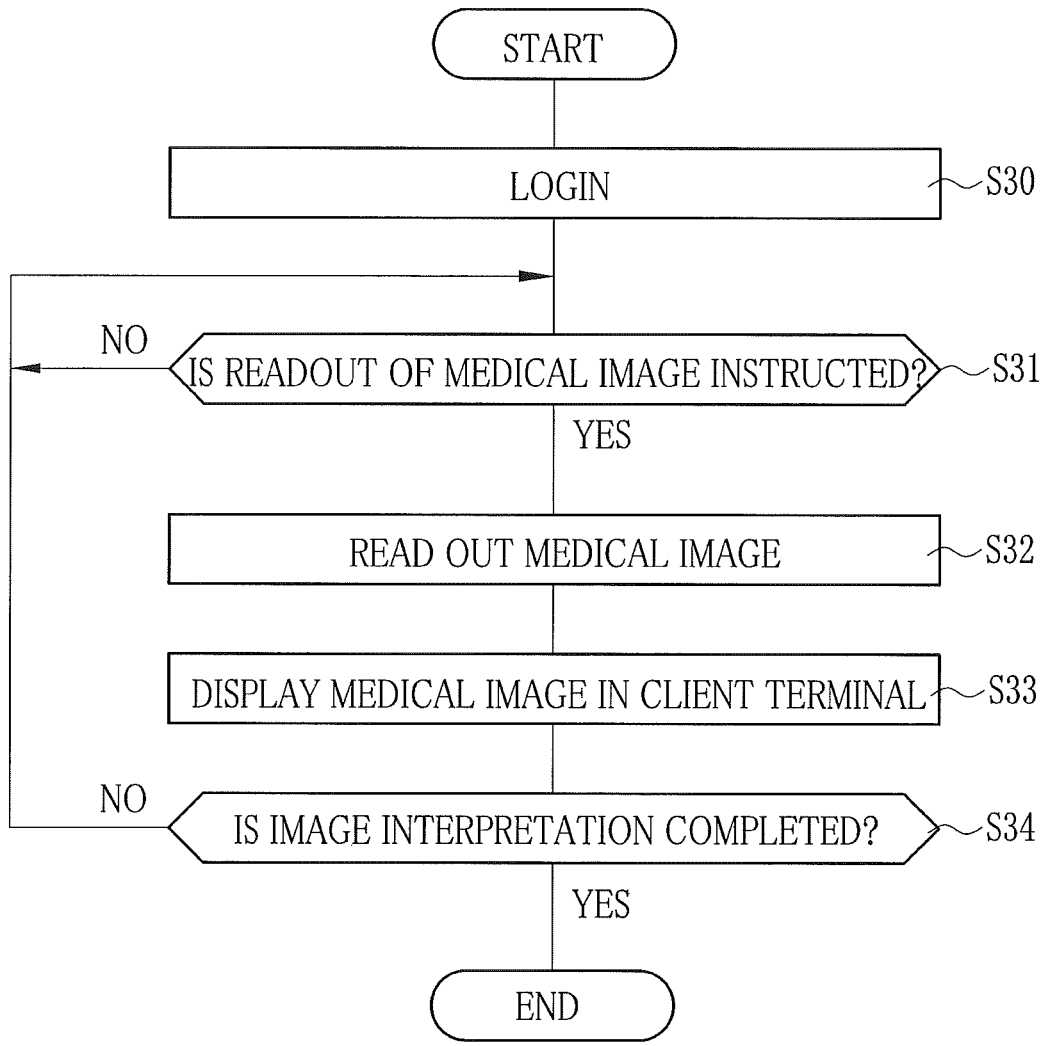
FIG. 12 is a flow chart illustrating steps of image interpretation of the medical image.

The operation of the medical image managing system is described now by referring to flow charts of FIGS. 5, 6 and 12. In FIG. 12, a doctor or physician for image interpretation accesses the image server 12 by login in the step S30 at the client terminal 13 which may be the image diagnosis apparatus 17 or the portable terminal apparatus 18 or 19. In case he or she manipulates for the login, the authenticator 46 in FIG. 3 causes the monitor 17a of the image diagnosis apparatus 17 or the touchscreen panel 41 of the portable terminal apparatus 18 or 19 to display an input menu for inputting a user ID for the login and password. Upon receiving the inputs of the user ID and the password from the user, the authenticator 46 transmits information of the login, the user ID and the password to the image server 12.

The authenticator 33 of the image server 12 in FIG. 2 compares the user ID and password transmitted from the client terminal 13 (for example, a particular one of the portable terminal apparatuses 18) with the user ID and password stored in the user information database 32. Assuming that the user information database 32 stores the user ID and password coinciding with those being transmitted, then the image server 12 authenticates the client terminal 13. Assuming that the user information database 32 does not store the user ID and password coinciding with those being transmitted, then the image server 12 does not authenticate the client terminal 13.

The authenticator 46 of the client terminal 13, in the case of an unsuccessful authentication in the image server 12, causes the monitor 17a of the image diagnosis apparatus 17 or the touchscreen panel 41 of the portable terminal apparatus 18 or 19 to display an input menu of a user ID and password for login, so as to encourage the login for a second time.

In case the client terminal 13 is manipulated for image interpretation of a medical image (yes in the step S31), read-out of the medical image is started in the step S32 for reading out the medical image from the image server 12 for display on the client terminal 13. In FIG. 5, the image acquisition device 47 of the client terminal 13 in the readout of medical image transmits a medical image request to the image server 12 in the step S1. The medical image request includes request information of a patient ID and the like specified by a user. The image server 12 upon receiving the medical image request transmitted by the client terminal 13 transmits the measurement data 68 of FIG. 7 to the client terminal 13 in the step S2.

The communication speed measurer 50 acquires the communication speed CS between the image server 12 and the client terminal 13 in the step S3 according to a reception time point RT of receiving the measurement data 68 and a start time point BT of transmitting the measurement data 68. The processing speed measurer 51 (corresponding to a processing speed detector) causes the density converter 54 (for contrast enhancement) in the image processor 48 to perform the density conversion of the measurement image 68a of the measurement data 68, to acquire the processing speed PS (namely, PS1 or PS2) of the density converter 54 in the step S4.

The communication speed CS and processing speed PS are transmitted from the client terminal 13 to the image server 12 in the step S5. The density conversion mode checker 35 of the image server 12 functions according to the communication speed CS and the processing speed PS received from the client terminal 13 and the processing speed PS3 of the density converter 38 of the image server 12 read from the memory, and checks which of the first and second density conversion modes for use in the density conversion of a medical image makes it possible more quickly to display a density-converted medical image at the client terminal 13 in the step S6.

Assuming that the first density conversion mode is selected in the density conversion mode checker 35, the density converter 38 (for contrast enhancement) of the image server 12 performs the density conversion of a medical image in the step S7. A density-converted medical image after the density conversion in the density converter 38 is transmitted from the image server 12 to the client terminal 13 in the step S8. The density-converted medical image transmitted to the client terminal 13 is displayed in the image display field 65 of the medical image screen area 57 in FIG. 4 by the image display controller 49 in the step S9.

Assuming that the second density conversion mode is selected in the density conversion mode checker 35, the image decomposition processing device 39 of the image server 12 performs decomposition processing of decomposing a medical image into a higher bit image G1 (8 higher bit planes) and a lower bit image G2 (8 lower bit planes) in the step S10. The image server 12 transmits the higher bit image G1 and the lower bit image G2 serially to the client terminal 13 in the steps S11 and S12. The client terminal 13 upon receiving the higher bit image G1 and the lower bit image G2 from the image server 12 causes the image synthesizing device 53 of the image processor 48 to synthesize the higher bit image G1 and the lower bit image G2 to reconstruct the medical image 72 as an original in the step S13. The density converter 54 of the client terminal 13 performs the density conversion of the medical image to generate a density-converted medical image in the step S14. The density-converted medical image from the density converter 54 is displayed in the image display field 65 of the medical image screen area 57 in FIG. 4 by the image display controller 49 of the client terminal 13 in the step S9.

In FIG. 12, the client terminal 13 displays the medical image in the step S33. A doctor or physician can interpret the medical image with the client terminal 13. To finish the image interpretation of the medical image at the client terminal 13 (yes in the step S34), the image viewer operating in the client terminal 13 is shut down. Assuming that image interpretation of another medical image is performed, the image viewer reads out the medical image (no in the step S34).

Consequently, the density-converted medical image can be displayed rapidly at the client terminal 13, because the density conversion of the medical image is possible by comparing processing time in use of the first density conversion mode and that in use of the second density conversion mode and by selecting one of the density conversion modes with the shorter processing time.

The communication speed between the image server 12 and the client terminal 13 is likely to change due to an increase in the communication traffic, difficulties in networked devices, or the like. Specially, the wireless LAN 22 and telephone lines of the mobile telephone are easily influenced by a communication state depending upon radio waves in particular locations of communication. However, the client terminal 13 in the present embodiment measures the communication speed and processing speed, to select a density conversion mode according to the measured values. It is possible rapidly to display a density-converted medical image at the client terminal 13 in compliance with changes in the communication state in a flexible manner.

Assuming that the density conversion mode is changed over to the second density conversion mode for the density conversion at the client terminal 13, a medical image is decomposed into a higher bit image G1 and a lower bit image G2 before transmission to the client terminal 13. The medical image can be displayed even by the image viewer based on the browser.

In the first embodiment, the client terminal 13 measures the communication speed. However, it is possible to measure the communication speed in the image server 12 to be disclosed in a second embodiment. For the image server 12 to measure the communication speed, a medical image request from the client terminal 13 to the image server 12, for example, can be caused to include information of a start time point of transmission in a manner similar to the measurement data 68. The image server 12 acquires communication time of the medical image request according to a reception time point of the medical image request and the start time point of the transmission included in the medical image request. The communication speed can be measured according to the communication time and the data size of the medical image request.

Second Embodiment

In the first embodiment, the measurement image 68a of the measurement data 68 transmitted from the image server 12 to the client terminal 13 is processed in the density conversion actually by the density converter 54 of the client terminal 13, to measure the processing speed of the client terminal 13. In contrast, the image server 12 in a second embodiment detects a processing speed of the client terminal 13 according to device-specific information (recognition information) transmitted from the client terminal 13 to the image server 12. Elements similar to those of the first embodiments are designated with identical reference numerals.

Figure 13:
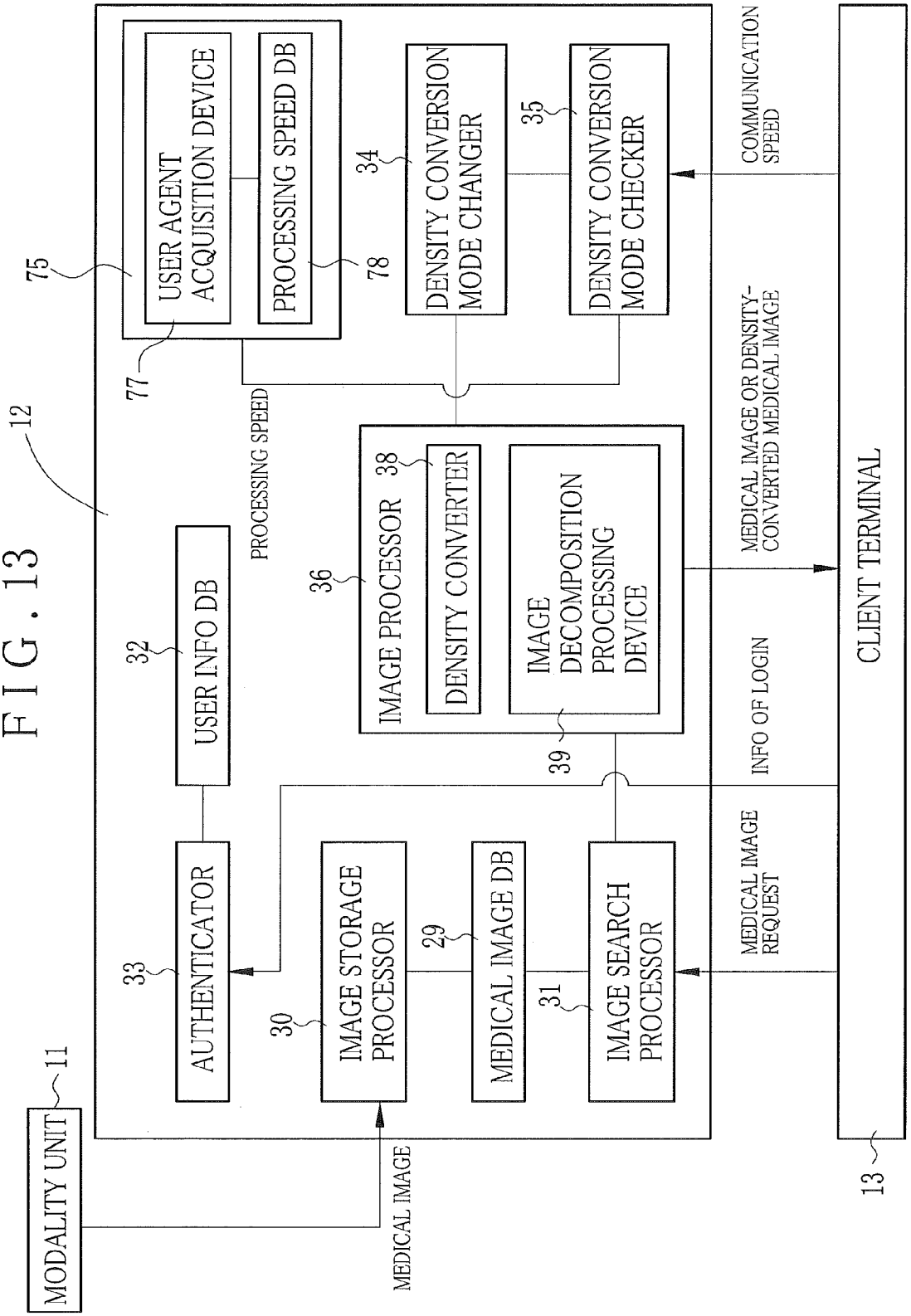
FIG. 13 is a block diagram schematically illustrating functional arrangement of an image server of a second embodiment.
Figure 14:
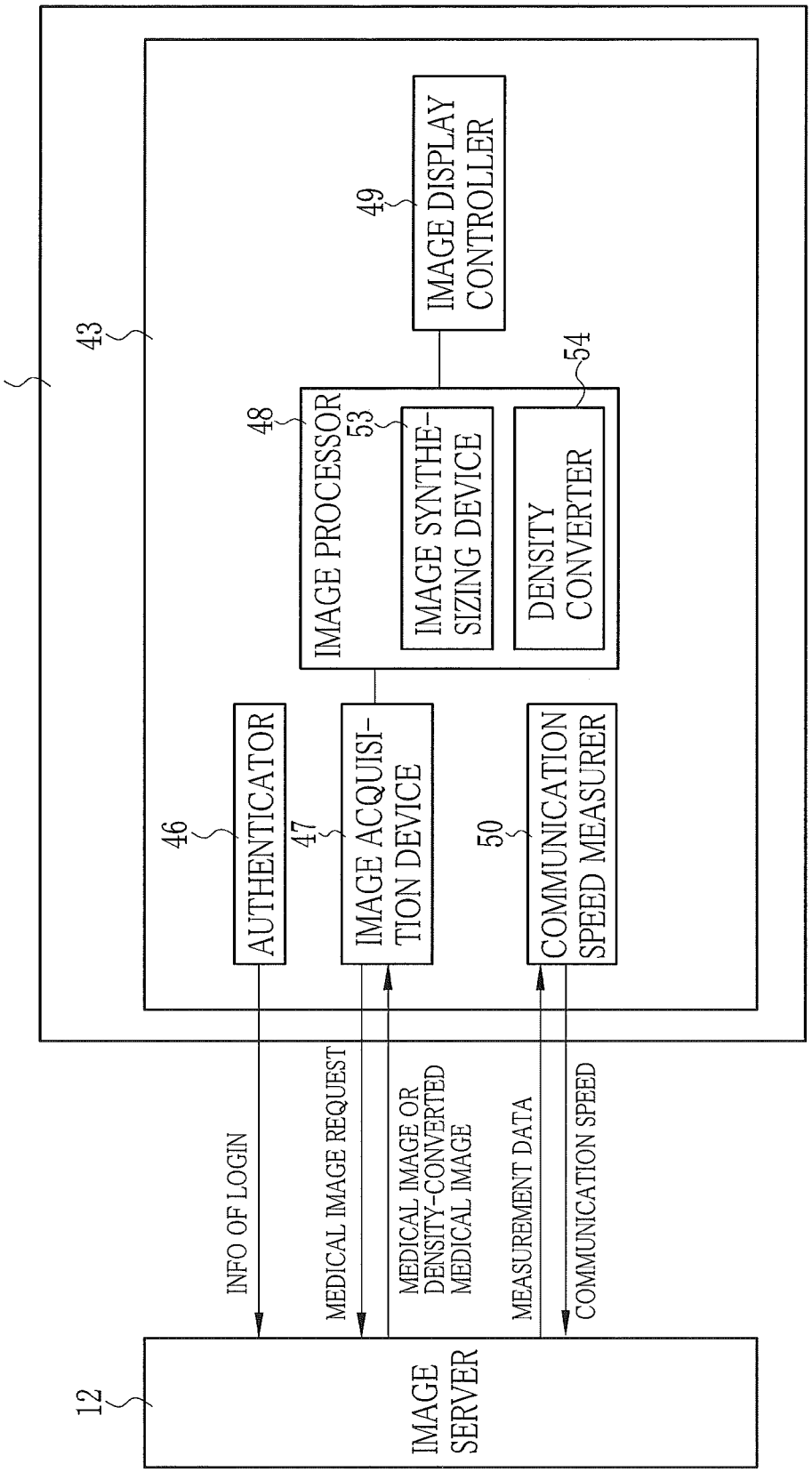
FIG. 14 is a block diagram schematically illustrating functional arrangement of a client terminal of the second embodiment.
Figure 15:
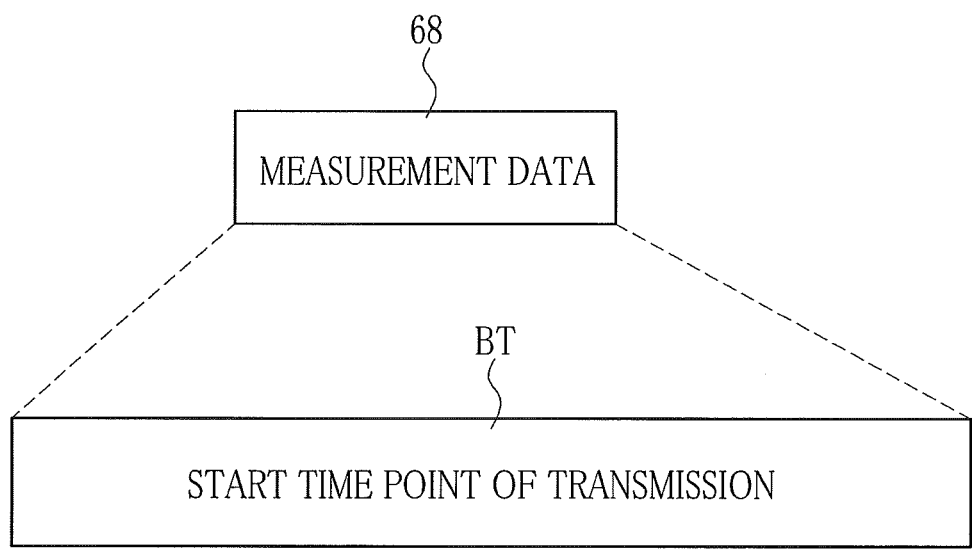
FIG. 15 is an explanatory view illustrating a structure of measurement data in the second embodiment.

In FIG. 13, the image server 12 has a processing speed detector 75 for detecting a processing speed of the client terminal 13 according to device-specific information transmitted from the client terminal 13 to the image server 12. As illustrated in FIG. 14, the client terminal 13 does not have a processing speed measurer. In the second embodiment, no measurement of the processing speed is performed in the client terminal 13. The measurement data 68 does not include a measurement image as illustrated in FIG. 15.

A web browser of a general type including the browser 43 of the client terminal 13 transmits a data request for requesting readout of data to a server. The data request includes a distinguished name of a user agent. The user agent is software or hardware used for utilizing requested data, for example, includes a browser name, type name of the client terminal, and the like. Also, the browser 43 of the second embodiment transmits the distinguished name of the user agent simultaneously upon transmitting a medical image request as a data request to the image server 12.

The processing speed detector 75 of the image server 12 includes a user agent acquisition device 77 and a processing speed database 78 (storage medium). The user agent acquisition device 77 acquires a user agent or user agent information as device-specific information of the client terminal 13 from the medical image request transmitted from the browser 43 of the client terminal 13. An example of the user agent information includes a browser name of the browser 43, and a distinguished name, such as a type name of the client terminal 13 and the like.

In FIG. 16, a table 80 is illustrated, with which the processing speed database 78 stores values of the processing speed of the density conversion obtained by combinations of browser names and type names. The processing speed detector 75 performs search in the processing speed database 78 according to the browser name and the type name of the client terminal acquired by the user agent acquisition device 77, and specifies a relevant value of the processing speed. The specified processing speed from the processing speed detector 75 is used for detecting a density conversion mode in the density conversion mode checker 35 in a manner similar to the first embodiment.

In the second embodiment, the image server 12 detects the processing speed at the client terminal 13, in which measurement of the processing speed can be unnecessary. As a result, processing time required for displaying a medical image at the client terminal 13 can be shortened, because a measurement image can be omitted from the measurement data 68.

Third Embodiment

In the first embodiment, the higher bit image G1 and the lower bit image G2 decomposed from the medical image 72 are transmitted from the image server 12 to the client terminal 13 in an unchanged manner in the second density conversion mode. In a third embodiment, the higher bit image G1 and the lower bit image G2 are compressed and then transmitted from the image server 12 to the client terminal 13. Elements similar to those of the first embodiment are designated with identical reference numerals.

Figure 17:
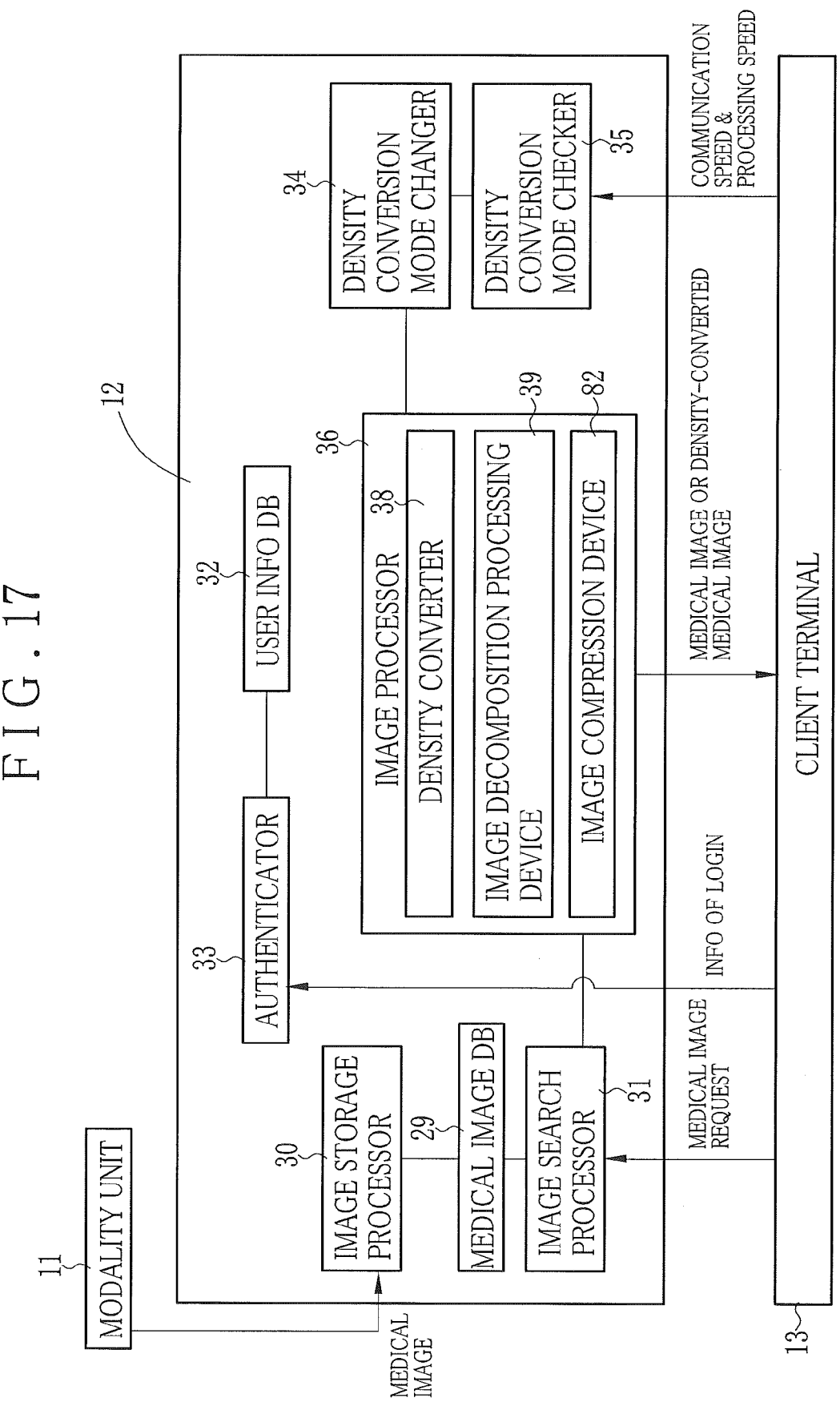
FIG. 17 is a block diagram schematically illustrating functional arrangement of an image server of a third embodiment.
Figure 18:
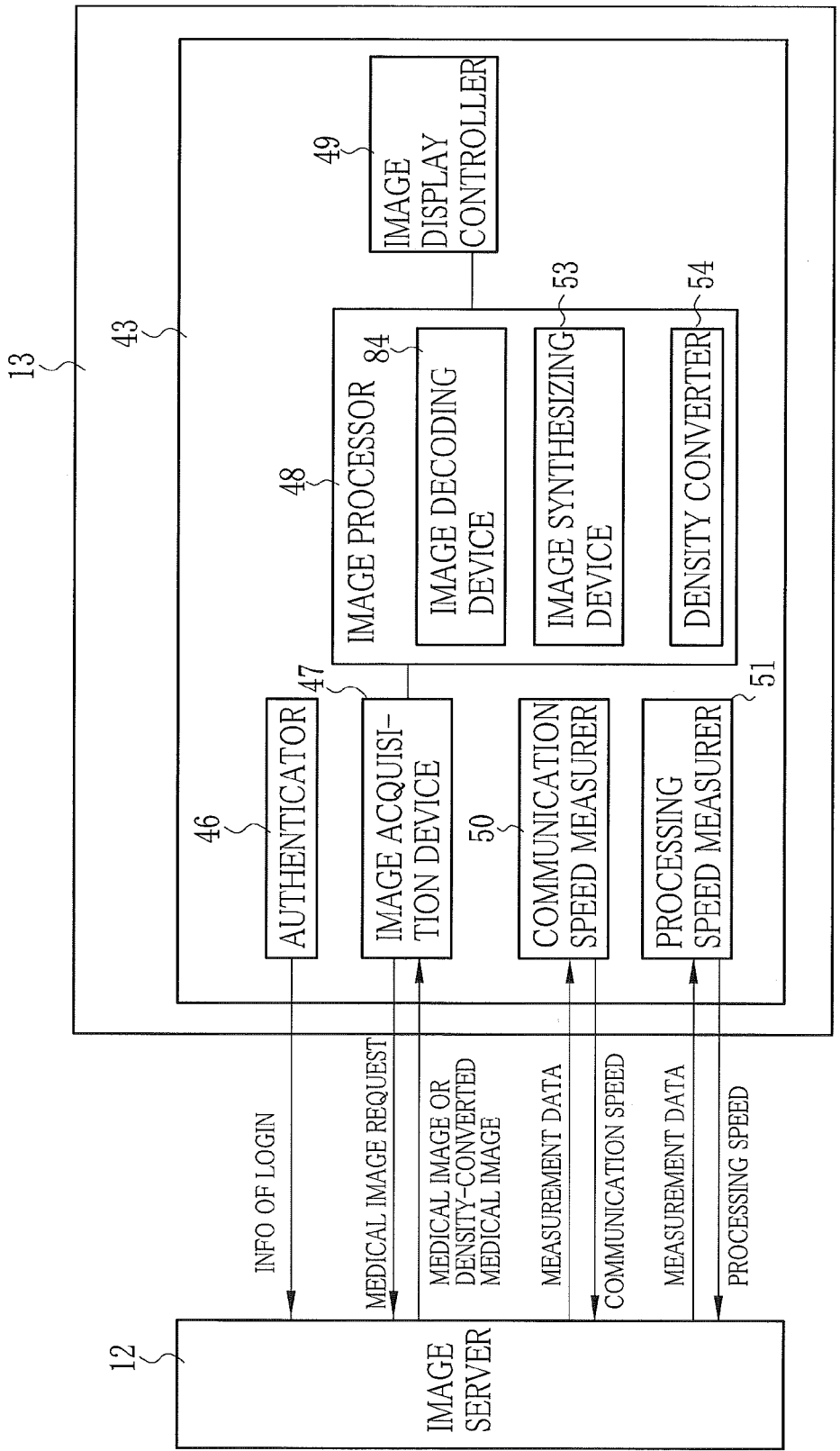
FIG. 18 is a block diagram schematically illustrating functional arrangement of a client terminal of the third embodiment.
Figure 19:
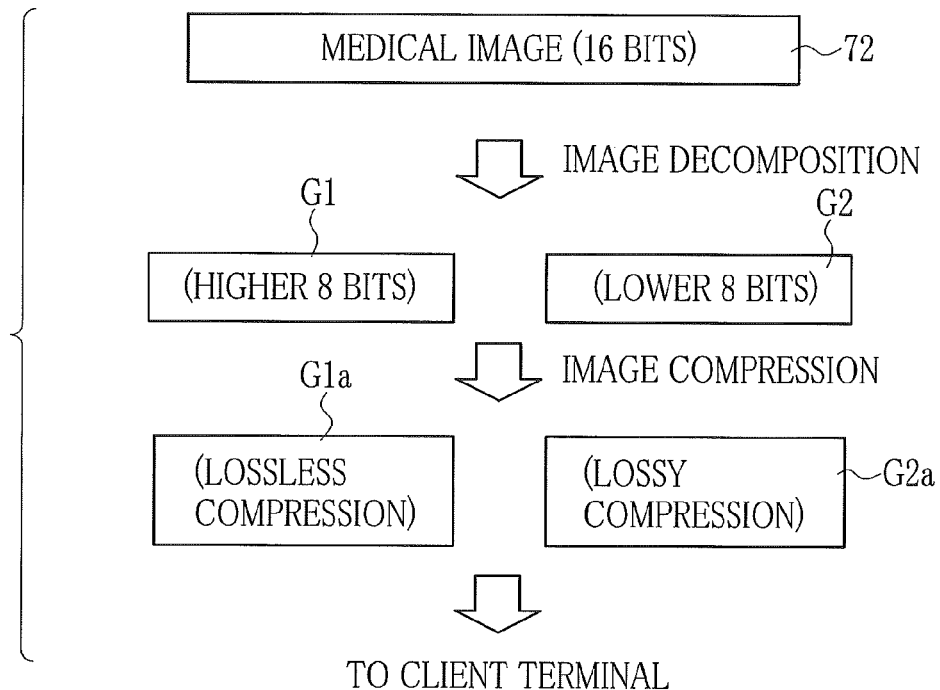
FIG. 19 is a schematic view illustrating steps of image decomposition in the third embodiment.

In FIG. 17, an image compression device 82 is incorporated in the image processor 36 of the image server 12. In FIG. 18, an image decoding device 84 is incorporated in the image processor 48 of the client terminal 13. In FIG. 19, the image compression device 82 of the image server 12 compresses the higher bit image G1 (8 higher bit planes) in lossless compression (reversible compression) to obtain a first compressed component image G1a, and compresses the lower bit image G2 (8 lower bit planes) in lossy compression (irreversible compression) to obtain a second compressed component image G2a, the higher bit image G1 being one of those decomposed by the image decomposition processing device 39 and having larger influence to visual recognition of a medical image. The image server 12 transmits the first compressed component image G1a and the second compressed component image G2a to the client terminal 13.

Figure 20:
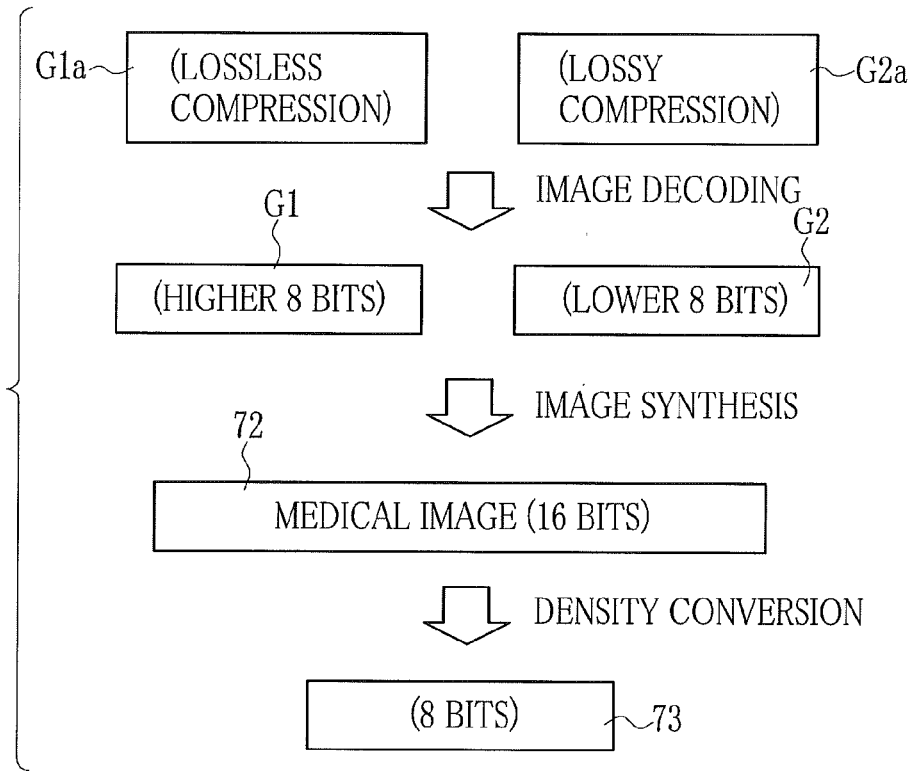
FIG. 20 is a schematic view illustrating steps of density conversion of the decomposed images in the third embodiment.

In FIG. 20, the image decoding device 84 of the client terminal 13 decodes the first compressed component image G1a and the second compressed component image G2a compressed by the image compression device 82 to the higher bit image G1 and the lower bit image G2. The higher bit image G1 and the lower bit image G2 after decoding are synthesized together by the image synthesizing device 53, and processed by the density converter 54 in the density conversion.

In the third embodiment, the first compressed component image G1a and the second compressed component image G2a are transmitted from the image server 12 to the client terminal 13 in the second density conversion mode after compressing the higher bit image G1 and the lower bit image G2, so that the communication time can be shortened. A first one of the higher bit image G1 and the lower bit image G2 with higher influence to visual recognition of the medical image is compressed in lossless compression. A second one of the higher bit image G1 and the lower bit image G2 is compressed in lossy compression. It is possible to minimize the communication time with maintained image quality of the medical image.

Among the higher bit image G1 and the lower bit image G2, the higher bit image G1 is compressed in lossless compression, and the lower bit image G2 is compressed in lossy compression. However, it is possible to compress the lower bit image G2 in lossless compression and the higher bit image G1 in lossy compression, typically in case influence of the lower bit image G2 to the visual recognition of the medical image is larger.

Fourth Embodiment

In the first embodiment, the higher bit image G1 and lower bit image G2 decomposed from the medical image 72 are transmitted from the image server 12 to the client terminal 13 in the second density conversion mode in a sequence of the higher bit image G1 and lower bit image G2. In a fourth embodiment, a sequence of transmitting the higher bit image G1 and lower bit image G2 is in reverse. Elements similar to those of the first embodiments are designated with identical reference numerals.

Figure 21:
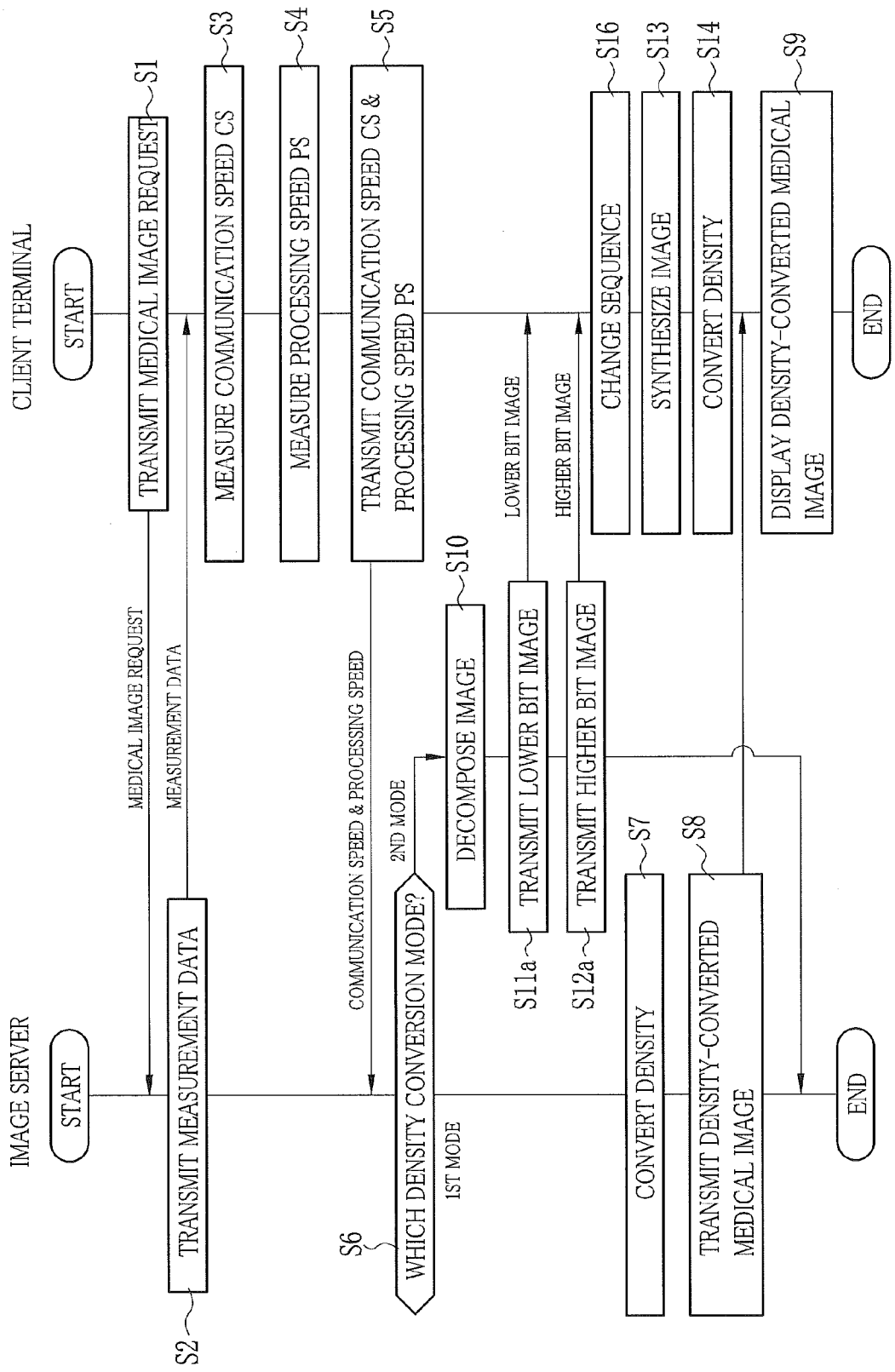
FIG. 21 is a flow chart illustrating detection of detecting the density conversion modes and steps in the density conversion modes in a fourth embodiment.

In FIGS. 21 and 22, the image server 12 transmits the lower bit image G2 and then the higher bit image G1 serially in the steps S11a and S12a to the client terminal 13 after their decomposition by the image decomposition processing device 39. In FIGS. 21 and 23, the image synthesizing device 53 of the client terminal 13 changes a sequence of the images to a set of the higher bit image G1 and the lower bit image G2 in the step S16, and then performs the synthesis in the step S13. Thus, it is impossible to reconstruct the medical image even upon viewing the images in a stealth mode in the course of transmission from the image server 12 to the client terminal 13, because the sequence of the images is changed. Theft of personal information by viewing the medical image in the stealth mode can be prevented.

In each of the above embodiments, the medical image is decomposed into higher and lower bit images in the second density conversion mode. However, it is possible to decompose the medical image into three or more images in a condition under an upper limit of a bit number processable in the browser 43 of the client terminal 13. The use of the decomposition into three or more images in the fourth embodiment makes it more difficult to reconstruct an original medical image from the decomposed images. It is possible more reliably to prevent theft of personal information by viewing medical image in a stealth mode.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A medical image managing system having an image server for managing a plurality of a medical image, and a client terminal, connected to said image server in a networked arrangement, for causing a monitor to display a density-converted medical image obtained by density conversion of said medical image, said medical image managing system comprising:
   a communication speed measurer which measures a communication speed between said image server and said client terminal;
   a processing speed detector which detects a processing speed of said client terminal for said density conversion;
   a density conversion mode checker which compares processing time of a first density conversion mode and processing time of a second density conversion mode after acquisition according to said communication speed measured by said communication speed measurer, said processing speed of said client terminal detected by said processing speed detector, and a predetermined processing speed of said image server, so as to select one of said density conversion modes with a shorter value of said processing time;
   an image processor which, upon selecting said first density conversion mode, transmits said density-converted medical image to said client terminal after said density conversion of said medical image in said image server, and, upon selecting said second density conversion mode, transmits said medical image to said client terminal to perform said density conversion of said medical image in said client terminal.

2. A medical image managing system as defined in claim 1, wherein said density conversion mode checker acquires:
   first density conversion time for said density conversion of said medical image in said image server;
   first communication time for transmitting said density-converted medical image from said image server to said client terminal;
   second communication time for transmitting said medical image from said image server to said client terminal;
   second density conversion time for said density conversion of said medical image in said client terminal;
   said density conversion mode checker compares said first mode processing time obtained by adding up said first density conversion time and said first communication time with said second mode processing time obtained by adding up said second density conversion time and said second communication time.

3. A medical image managing system as defined in claim 1, wherein said processing speed detector measures said processing speed of said client terminal for said density conversion.

4. A medical image managing system as defined in claim 2, wherein said processing speed detector measures said processing speed of said client terminal for said density conversion.

5. A medical image managing system as defined in claim 3, wherein said processing speed detector causes said client terminal to perform said density conversion of a measurement image, and measures said processing time according to a data size of said measurement image and time taken for said density conversion.

6. A medical image managing system as defined in claim 1, wherein said processing speed detector detects said processing speed of said client terminal for said density conversion according to device-specific information of said client terminal transmitted from said client terminal to said image server.

7. A medical image managing system as defined in claim 2, wherein said processing speed detector detects said processing speed of said client terminal for said density conversion according to device-specific information of said client terminal transmitted from said client terminal to said image server.

8. A medical image managing system as defined in claim 1, wherein said communication speed measurer causes said image server and said client terminal to communicate with measurement data, and measures said communication speed according to a data size of said measurement data and time taken for communication of said measurement data.

9. A medical image managing system as defined in claim 2, wherein said communication speed measurer causes said image server and said client terminal to communicate with measurement data, and measures said communication speed according to a data size of said measurement data and time taken for communication of said measurement data.

10. A medical image managing system as defined in claim 1, wherein said image server includes an image decomposition processing device for decomposing said medical image into at least a higher bit image of higher order bits of gradation levels of said medical image and a lower bit image of lower order bits of said gradation levels of said medical image;
  in said second density conversion mode, said higher bit image and said lower bit image decomposed by said image decomposition processing device are transmitted to said client terminal.

11. A medical image managing system as defined in claim 2, wherein said image server includes an image decomposition processing device for decomposing said medical image into at least a higher bit image of higher order bits of gradation levels of said medical image and a lower bit image of lower order bits of said gradation levels of said medical image;
  in said second density conversion mode, said higher bit image and said lower bit image decomposed by said image decomposition processing device are transmitted to said client terminal.

12. A medical image managing system as defined in claim 10, wherein a bit number of said higher bit image and said lower bit image is equal to or less than an upper limit of a bit number processable in said client terminal as an image.

13. A medical image managing system as defined in claim 10, wherein said image server compresses a first one of said higher bit image and said lower bit image with larger influence to visual recognition of said medical image in lossless compression, and compresses a remaining one of said higher bit image and said lower bit image in lossy compression, before transmission of said higher bit image and said lower bit image to said client terminal.

14. A medical image managing system as defined in claim 10, wherein said client terminal reconstructs said medical image by synthesizing said higher bit image and said lower bit image, and performs said density conversion of said medical image being reconstructed.

15. A medical image managing system as defined in claim 14, wherein said image server transmits said lower bit image to said client terminal before transmitting said higher bit image to said client terminal;
  said client terminal changes a sequence of said lower bit image and said higher bit image before synthesizing said higher bit image with said lower bit image.

16. A medical image managing method for a medical image managing system having an image server for managing a plurality of a medical image, and a client terminal, connected to said image server in a networked arrangement, for causing a monitor to display a density-converted medical image obtained by density conversion of said medical image, said medical image managing method comprising steps of:
  measuring a communication speed between said image server and said client terminal;
  detecting a processing speed of said client terminal for said density conversion;
  comparing processing time of a first density conversion mode and processing time of a second density conversion mode after acquisition according to said communication speed, said processing speed of said client terminal, and a predetermined processing speed of said image server, so as to select one of said density conversion modes with a shorter value of said processing time;
  upon selecting said first density conversion mode, transmitting said density-converted medical image to said client terminal after said density conversion of said medical image in said image server, and upon selecting said second density conversion mode, transmitting said medical image to said client terminal to perform said density conversion of said medical image in said client terminal.

\* \* \* \* \*